United States Patent
McCormack et al.

(10) Patent No.: US 11,559,408 B2
(45) Date of Patent: Jan. 24, 2023

(54) METHODS AND APPARATUS FOR ACCESSING AND TREATING THE FACET JOINT

(71) Applicant: PROVIDENCE MEDICAL TECHNOLOGY, INC., Pleasanton, CA (US)

(72) Inventors: Bruce M. McCormack, San Francisco, CA (US); Nathan Christopher Maier, Hayward, CA (US)

(73) Assignee: Providence Medical Technology, Inc., Pleasanton, CA (US)

( * ) Notice: Subject to any disclaimer, the term of this patent is extended or adjusted under 35 U.S.C. 154(b) by 0 days.

(21) Appl. No.: 17/035,835

(22) Filed: Sep. 29, 2020

(65) Prior Publication Data
US 2021/0022881 A1 Jan. 28, 2021

Related U.S. Application Data

(63) Continuation of application No. 15/467,773, filed on Mar. 23, 2017, now abandoned, which is a (Continued)

(51) Int. Cl.
*A61F 2/44* (2006.01)
*A61B 17/16* (2006.01)
(Continued)

(52) U.S. Cl.
CPC ...... *A61F 2/4405* (2013.01); *A61B 17/00234* (2013.01); *A61B 17/1604* (2013.01);
(Continued)

(58) Field of Classification Search
CPC ............ A61B 17/1671; A61B 17/7074; A61B 17/00234; A61B 17/1604; A61B 17/1659; A61B 2017/0256; A61B 17/3211; A61F 2/4405; A61F 2/4601; A61F 2/4611; A61F 2/4455

See application file for complete search history.

(56) References Cited

U.S. PATENT DOCUMENTS

| 1,934,962 A | 11/1933 | Barry |
| 2,708,376 A | 5/1955 | Booth |

(Continued)

FOREIGN PATENT DOCUMENTS

| DE | G9304368.6 U1 | 5/2003 |
| FR | 2722980 A1 | 2/1996 |

(Continued)

OTHER PUBLICATIONS

US 7,063,700 B2, 06/2006, Michelson (withdrawn)
(Continued)

*Primary Examiner* — Christopher D. Prone
(74) *Attorney, Agent, or Firm* — Dorsey & Whitney LLP

(57) ABSTRACT

Methods and systems are disclosed for accessing and treating the interior of the facet joint for vertebral distraction and immobilization. The systems include a number of tools that facilitate access to the facet joint, distraction of the articulating decortication of the articulating surfaces, and delivery of implants and agents into the facet joint for fusion.

6 Claims, 20 Drawing Sheets

Related U.S. Application Data continuation of application No. 14/675,626, filed on Mar. 31, 2015, now abandoned, which is a continuation of application No. 12/350,609, filed on Jan. 8, 2009, now Pat. No. 9,005,288.

(60) Provisional application No. 61/020,082, filed on Jan. 9, 2008.

(51) Int. Cl.

| | | |
|---|---|---|
| *A61F 2/28* | (2006.01) | |
| *A61F 2/46* | (2006.01) | |
| *A61B 17/00* | (2006.01) | |
| *A61B 17/3211* | (2006.01) | |
| *A61B 17/70* | (2006.01) | |
| *A61B 17/02* | (2006.01) | |
| *A61F 2/30* | (2006.01) | |

(52) U.S. Cl.
 CPC ...... *A61B 17/1659* (2013.01); *A61B 17/1671* (2013.01); *A61B 17/3211* (2013.01); *A61B 17/7074* (2013.01); *A61F 2/28* (2013.01); *A61F 2/4601* (2013.01); *A61F 2/4611* (2013.01); *A61B 2017/0256* (2013.01); *A61F 2/441* (2013.01); *A61F 2/4455* (2013.01); *A61F 2002/30616* (2013.01); *A61F 2310/00359* (2013.01)

(56) References Cited

U.S. PATENT DOCUMENTS

| | | |
|---|---|---|
| 2,984,241 A | 5/1961 | Carlson |
| 3,486,505 A | 12/1969 | Morrison |
| 4,479,491 A | 10/1984 | Martin |
| 4,530,355 A | 7/1985 | Griggs |
| 4,604,995 A | 8/1986 | Stephens et al. |
| 4,772,287 A | 9/1988 | Ray et al. |
| 4,877,020 A | 10/1989 | Vich |
| 4,878,915 A | 11/1989 | Brantigan |
| 5,015,247 A | 5/1991 | Michelson |
| 5,026,373 A | 6/1991 | Ray et al. |
| 5,100,405 A | 3/1992 | McLaren |
| 5,135,528 A | 8/1992 | Winston |
| 5,192,327 A | 3/1993 | Brantigan |
| 5,236,460 A | 8/1993 | Barber |
| 5,443,514 A | 8/1995 | Steffee |
| 5,484,437 A | 1/1996 | Michelson |
| 5,489,307 A | 2/1996 | Kuslich et al. |
| 5,505,732 A | 4/1996 | Michelson |
| 5,527,312 A | 6/1996 | Ray |
| 5,549,679 A | 8/1996 | Kuslich et al. |
| 5,554,191 A | 9/1996 | Lahille et al. |
| 5,571,109 A | 11/1996 | Bertagnoli |
| 5,571,191 A | 11/1996 | Fitz |
| 5,584,832 A | 12/1996 | Schlapfer et al. |
| 5,593,409 A | 1/1997 | Michelson |
| 5,632,747 A | 5/1997 | Scarborough et al. |
| 5,649,945 A * | 7/1997 | Ray ............... A61B 17/320016 606/167 |
| 5,653,763 A | 8/1997 | Errico et al. |
| 5,665,122 A | 9/1997 | Kambin |
| 5,674,295 A | 10/1997 | Ray et al. |
| 5,720,748 A | 2/1998 | Kuslich et al. |
| 5,741,253 A | 4/1998 | Michelson |
| 5,772,661 A | 6/1998 | Michelson |
| 5,792,044 A | 8/1998 | Foley et al. |
| 5,797,909 A | 8/1998 | Michelson |
| 5,836,948 A | 11/1998 | Zucherman et al. |
| 5,879,353 A | 3/1999 | Terry |
| 5,885,299 A | 3/1999 | Winslow et al. |
| 5,891,147 A * | 4/1999 | Moskovitz ........... A61B 17/025 606/79 |
| 5,895,426 A | 4/1999 | Scarborough et al. |
| 5,899,908 A | 5/1999 | Kuslich et al. |
| 5,928,238 A | 7/1999 | Scarborough et al. |
| 5,953,820 A | 9/1999 | Vasudeva |
| 5,961,522 A | 10/1999 | Mehdizadeh |
| 5,976,146 A | 11/1999 | Ogawa et al. |
| 6,008,433 A | 12/1999 | Stone |
| 6,033,405 A | 3/2000 | Winslow et al. |
| 6,045,580 A | 4/2000 | Scarborough et al. |
| 6,063,088 A | 5/2000 | Winslow |
| RE36,758 E | 6/2000 | Fitz |
| 6,080,155 A | 6/2000 | Michelson |
| 6,090,143 A | 7/2000 | Meriwether et al. |
| 6,096,038 A | 8/2000 | Michelson |
| 6,099,531 A | 8/2000 | Bonutti |
| 6,102,950 A | 8/2000 | Vaccaro |
| 6,113,602 A | 9/2000 | Sand |
| 6,149,650 A | 11/2000 | Michelson |
| RE37,005 E | 12/2000 | Michelson et al. |
| 6,159,245 A | 12/2000 | Meriwether et al. |
| 6,174,311 B1 | 1/2001 | Branch et al. |
| 6,176,882 B1 | 1/2001 | Biedermann et al. |
| 6,179,873 B1 | 1/2001 | Zientek |
| 6,190,388 B1 | 2/2001 | Michelson et al. |
| 6,190,414 B1 | 2/2001 | Young et al. |
| 6,193,757 B1 | 2/2001 | Foley et al. |
| 6,200,322 B1 | 3/2001 | Branch et al. |
| 6,210,412 B1 | 4/2001 | Michelson |
| RE37,161 E | 5/2001 | Michelson et al. |
| 6,224,595 B1 | 5/2001 | Michelson |
| 6,224,607 B1 | 5/2001 | Michelson |
| 6,224,630 B1 | 5/2001 | Bao et al. |
| 6,245,108 B1 | 6/2001 | Biscup |
| 6,248,110 B1 | 6/2001 | Reiley et al. |
| D444,878 S | 7/2001 | Walter |
| D445,188 S | 7/2001 | Walter |
| 6,264,656 B1 | 7/2001 | Michelson |
| 6,267,763 B1 | 7/2001 | Castro |
| 6,270,498 B1 | 8/2001 | Michelson |
| 6,283,966 B1 | 9/2001 | Boufburg |
| 6,315,795 B1 | 11/2001 | Scarborough et al. |
| 6,325,827 B1 | 12/2001 | Lin |
| 6,371,984 B1 | 4/2002 | Van Dyke et al. |
| 6,371,988 B1 | 4/2002 | Pafford et al. |
| 6,402,784 B1 | 6/2002 | Wardlaw |
| 6,423,063 B1 | 7/2002 | Bonutti |
| 6,423,083 B2 | 7/2002 | Reiley et al. |
| 6,425,919 B1 | 7/2002 | Lambrecht |
| 6,436,098 B1 | 8/2002 | Michelson |
| 6,436,142 B1 | 8/2002 | Paes et al. |
| 6,443,988 B2 | 9/2002 | Felt et al. |
| 6,451,023 B1 | 9/2002 | Salazar et al. |
| 6,454,807 B1 | 9/2002 | Jackson |
| 6,478,796 B2 | 11/2002 | Zucherman et al. |
| 6,500,206 B1 | 12/2002 | Bryan |
| 6,514,256 B2 | 2/2003 | Zucherman et al. |
| 6,524,312 B2 | 2/2003 | Landry et al. |
| 6,530,955 B2 | 3/2003 | Boyle et al. |
| 6,537,279 B1 | 3/2003 | Michelson |
| 6,558,390 B2 | 5/2003 | Cragg |
| 6,565,574 B2 | 5/2003 | Michelson |
| 6,565,605 B2 | 5/2003 | Fallin et al. |
| 6,569,186 B1 | 5/2003 | Winters et al. |
| 6,575,899 B1 | 6/2003 | Foley et al. |
| 6,575,919 B1 | 6/2003 | Reiley et al. |
| 6,575,979 B1 | 6/2003 | Cragg |
| 6,579,319 B2 | 6/2003 | Goble et al. |
| 6,582,432 B1 | 6/2003 | Michelson |
| 6,582,467 B1 | 6/2003 | Teitelbaum et al. |
| 6,607,530 B1 | 8/2003 | Carl et al. |
| 6,610,091 B1 | 8/2003 | Reiley |
| 6,626,905 B1 | 9/2003 | Schmiel et al. |
| 6,632,235 B2 | 10/2003 | Weikel et al. |
| 6,635,060 B2 | 10/2003 | Hanson et al. |
| 6,641,582 B1 | 11/2003 | Hanson et al. |
| 6,648,893 B2 | 11/2003 | Dudasik |
| 6,652,584 B2 | 11/2003 | Michelson |
| 6,663,647 B2 | 12/2003 | Reiley et al. |
| 6,666,866 B2 | 12/2003 | Martz et al. |
| 6,679,886 B2 | 1/2004 | Weikel et al. |

(56) References Cited

U.S. PATENT DOCUMENTS

| | | |
|---|---|---|
| 6,682,535 B2 | 1/2004 | Hoogland |
| 6,685,742 B1 | 2/2004 | Jackson |
| 6,709,458 B2 | 3/2004 | Michelson |
| 6,712,853 B2 | 3/2004 | Kuslich |
| 6,719,773 B1 | 4/2004 | Boucher et al. |
| 6,719,794 B2 | 4/2004 | Gerber et al. |
| 6,723,095 B2 | 4/2004 | Hammerslag |
| 6,733,534 B2 | 5/2004 | Sherman |
| 6,740,093 B2 | 5/2004 | Hochschuler et al. |
| 6,751,875 B2 | 6/2004 | Jones |
| 6,770,074 B2 | 8/2004 | Michelson |
| 6,793,679 B2 | 9/2004 | Michelson |
| 6,805,715 B2 | 10/2004 | Reuter et al. |
| 6,808,537 B2 | 10/2004 | Michelson |
| 6,814,738 B2 | 11/2004 | Naughton et al. |
| 6,823,871 B2 | 11/2004 | Schmieding |
| 6,840,941 B2 | 1/2005 | Rogers et al. |
| 6,851,430 B2 | 2/2005 | Tsou |
| 6,875,213 B2 | 4/2005 | Michelson |
| 6,899,719 B2 | 5/2005 | Reiley et al. |
| 6,921,403 B2 | 7/2005 | Cragg et al. |
| 6,923,813 B2 | 8/2005 | Phillips et al. |
| 6,958,077 B2 | 10/2005 | Suddaby |
| 6,962,606 B2 | 11/2005 | Michelson |
| 6,964,686 B2 | 11/2005 | Gordon |
| 6,966,930 B2 | 11/2005 | Arnin et al. |
| 6,972,035 B2 | 12/2005 | Michelson |
| 6,974,478 B2 | 12/2005 | Reiley et al. |
| 6,979,333 B2 | 12/2005 | Hammerslag |
| 6,986,772 B2 | 1/2006 | Michelson |
| 7,001,385 B2 | 2/2006 | Bonutti |
| 7,008,453 B1 | 3/2006 | Michelson |
| 7,033,362 B2 | 4/2006 | McGahan et al. |
| 7,033,392 B2 | 4/2006 | Schmiel et al. |
| 7,033,394 B2 | 4/2006 | Michelson |
| 7,066,961 B2 | 6/2006 | Michelson |
| D524,443 S | 7/2006 | Blain |
| 7,083,623 B2 | 8/2006 | Michelson |
| 7,090,698 B2 | 8/2006 | Fallin et al. |
| 7,096,972 B2 | 8/2006 | Orozco, Jr. |
| 7,101,398 B2 | 9/2006 | Dooris et al. |
| 7,115,128 B2 | 10/2006 | Michelson |
| 7,118,598 B2 | 10/2006 | Michelson |
| 7,128,760 B2 | 10/2006 | Michelson |
| 7,156,877 B2 | 1/2007 | Lotz et al. |
| 7,166,110 B2 | 1/2007 | Yundt |
| 7,175,023 B2 | 2/2007 | Martin |
| 7,179,263 B2 | 2/2007 | Zdeblick et al. |
| 7,207,991 B2 | 4/2007 | Michelson |
| D541,940 S | 5/2007 | Blain |
| 7,220,280 B2 | 5/2007 | Kast et al. |
| 7,255,703 B2 | 8/2007 | Mujwid et al. |
| 7,261,739 B2 | 8/2007 | Ralph et al. |
| 7,264,622 B2 | 9/2007 | Michelson |
| 7,273,498 B2 | 9/2007 | Bianchi et al. |
| 7,288,093 B2 | 10/2007 | Michelson |
| 7,291,149 B1 | 11/2007 | Michelson |
| 7,300,440 B2 | 11/2007 | Zdeblick et al. |
| 7,326,211 B2 | 2/2008 | Padget et al. |
| 7,326,214 B2 | 2/2008 | Michelson |
| 7,371,238 B2 | 5/2008 | Soboleski et al. |
| 7,399,303 B2 | 7/2008 | Michelson |
| 7,410,501 B2 | 8/2008 | Michelson |
| 7,431,722 B1 | 10/2008 | Michelson |
| 7,445,636 B2 | 11/2008 | Michelson |
| 7,452,359 B1 | 11/2008 | Michelson |
| 7,452,369 B2 | 11/2008 | Barry |
| 7,465,304 B2 | 12/2008 | Haufe et al. |
| 7,476,226 B2 | 1/2009 | Weikel et al. |
| 7,476,251 B2 | 1/2009 | Zucherman et al. |
| 7,479,160 B2 | 1/2009 | Branch et al. |
| 7,491,205 B1 | 2/2009 | Michelson |
| 7,491,240 B1 | 2/2009 | Carver et al. |
| 7,500,992 B2 | 3/2009 | Li |
| 7,517,358 B2 | 4/2009 | Peterson |
| 7,524,333 B2 | 4/2009 | Lambrecht et al. |
| 7,569,054 B2 | 8/2009 | Michelson |
| 7,569,057 B2 | 8/2009 | Liu et al. |
| 7,580,743 B2 | 8/2009 | Bourlion et al. |
| 7,591,851 B2 | 9/2009 | Winslow et al. |
| 7,601,170 B2 | 10/2009 | Winslow et al. |
| 7,608,077 B2 | 10/2009 | Cragg et al. |
| 7,608,107 B2 | 10/2009 | Michelson |
| 7,615,079 B2 | 11/2009 | Flickinger et al. |
| 7,618,451 B2 | 11/2009 | Berez et al. |
| 7,632,291 B2 | 12/2009 | Stephens et al. |
| 7,641,664 B2 | 1/2010 | Pagano |
| 7,648,509 B2 | 1/2010 | Stark |
| 7,648,523 B2 | 1/2010 | Mirkovic et al. |
| 7,655,027 B2 | 2/2010 | Michelson |
| 7,655,043 B2 | 2/2010 | Peterman et al. |
| 7,662,173 B2 | 2/2010 | Cragg et al. |
| D611,147 S | 3/2010 | Hanson et al. |
| 7,682,378 B2 | 3/2010 | Truckai et al. |
| 7,686,805 B2 | 3/2010 | Michelson |
| 7,686,807 B2 | 3/2010 | Padget et al. |
| 7,699,878 B2 | 4/2010 | Pavlov et al. |
| D615,653 S | 5/2010 | Horton |
| 7,708,761 B2 | 5/2010 | Petersen |
| 7,722,619 B2 | 5/2010 | Michelson |
| D619,719 S | 7/2010 | Pannu |
| D620,113 S | 7/2010 | Courtney et al. |
| 7,763,024 B2 | 7/2010 | Bertagnoli et al. |
| 7,763,050 B2 | 7/2010 | Winslow et al. |
| 7,776,090 B2 | 8/2010 | Winslow et al. |
| D623,748 S | 9/2010 | Horton et al. |
| D623,749 S | 9/2010 | Horton et al. |
| 7,789,898 B2 | 9/2010 | Peterman |
| D627,468 S | 11/2010 | Richter et al. |
| 7,824,431 B2 | 11/2010 | McCormack |
| 7,837,713 B2 | 11/2010 | Peterson |
| 7,846,183 B2 | 12/2010 | Blain |
| 7,846,184 B2 | 12/2010 | Sasso et al. |
| 7,850,733 B2 | 12/2010 | Baynham et al. |
| 7,862,589 B2 | 1/2011 | Thramann |
| 7,867,277 B1 | 1/2011 | Tohmeh |
| D631,967 S | 2/2011 | Horton |
| 7,879,098 B1 | 2/2011 | Simmons, Jr. |
| 7,887,565 B2 | 2/2011 | Michelson |
| 7,892,261 B2 | 2/2011 | Bonutti |
| 7,892,286 B2 | 2/2011 | Michelson |
| 7,896,803 B2 | 3/2011 | Schara et al. |
| 7,896,903 B2 | 3/2011 | Link |
| 7,901,439 B2 | 3/2011 | Horton |
| 7,914,530 B2 | 3/2011 | Michelson |
| 7,918,891 B1 | 4/2011 | Curran et al. |
| 7,922,729 B2 | 4/2011 | Michelson |
| 7,922,766 B2 | 4/2011 | Grob et al. |
| 7,935,136 B2 | 5/2011 | Alamin et al. |
| 7,938,857 B2 | 5/2011 | Krueger et al. |
| 7,942,903 B2 | 5/2011 | Moskowitz et al. |
| 7,988,712 B2 | 8/2011 | Hale et al. |
| 7,988,714 B2 | 8/2011 | Puekert et al. |
| 7,998,174 B2 | 8/2011 | Malandain et al. |
| 8,007,534 B2 | 8/2011 | Michelson |
| 8,029,540 B2 | 10/2011 | Winslow et al. |
| 8,043,334 B2 | 10/2011 | Fisher et al. |
| 8,052,728 B2 | 11/2011 | Hestad |
| 8,062,303 B2 | 11/2011 | Berry et al. |
| 8,066,705 B2 | 11/2011 | Michelson |
| D650,481 S | 12/2011 | Gottlieb et al. |
| 8,097,034 B2 | 1/2012 | Michelson |
| 8,100,944 B2 | 1/2012 | Lauryssen et al. |
| D653,757 S | 2/2012 | Binder |
| 8,114,158 B2 | 2/2012 | Carl et al. |
| 8,118,838 B2 | 2/2012 | Winslow et al. |
| 8,128,660 B2 | 3/2012 | Mitchel et al. |
| 8,133,261 B2 | 3/2012 | Fisher et al. |
| 8,142,503 B2 | 3/2012 | Malone |
| 8,147,553 B2 | 4/2012 | Vresilovic et al. |
| 8,162,981 B2 | 4/2012 | Vestgaarden |
| 8,172,877 B2 | 5/2012 | Winslow et al. |
| 8,177,872 B2 | 5/2012 | Nelson et al. |
| 8,197,513 B2 | 6/2012 | Fisher et al. |

(56) References Cited

U.S. PATENT DOCUMENTS

| | | |
|---|---|---|
| 8,206,418 B2 | 6/2012 | Triplett et al. |
| 8,267,966 B2 | 9/2012 | McCormack et al. |
| D674,900 S | 1/2013 | Janice et al. |
| 8,348,979 B2 | 1/2013 | McCormack |
| 8,361,152 B2 | 1/2013 | McCormack et al. |
| 8,366,748 B2 | 2/2013 | Kleiner |
| 8,382,767 B2 | 2/2013 | Wassinger et al. |
| D677,791 S | 3/2013 | Danacioglu et al. |
| 8,394,107 B2 | 3/2013 | Fanger et al. |
| 8,394,129 B2 | 3/2013 | Morgenstern et al. |
| D681,205 S | 4/2013 | Farris et al. |
| 8,425,558 B2 | 4/2013 | McCormack et al. |
| 8,439,922 B1 | 5/2013 | Arnold et al. |
| 8,512,347 B2 | 8/2013 | McCormack et al. |
| 8,523,908 B2 | 9/2013 | Malone |
| 8,529,609 B2 | 9/2013 | Helgerson et al. |
| 8,623,054 B2 | 1/2014 | Mccormack et al. |
| 8,668,722 B2 | 3/2014 | Pavlov et al. |
| 8,753,345 B2 | 6/2014 | McCormack et al. |
| 8,753,347 B2 | 6/2014 | McCormack et al. |
| 8,764,755 B2 | 7/2014 | Michelson |
| 8,828,062 B2 | 9/2014 | McCormack et al. |
| 8,834,530 B2 | 9/2014 | McCormack |
| 8,845,727 B2 | 9/2014 | Gottlieb et al. |
| 8,870,882 B2 | 10/2014 | Kleiner |
| D723,690 S | 3/2015 | McCormack et al. |
| D723,691 S | 3/2015 | McCormack et al. |
| 8,998,905 B2 | 4/2015 | Marik et al. |
| 9,005,288 B2 | 4/2015 | McCormack et al. |
| 9,011,492 B2 | 4/2015 | McCormack et al. |
| D732,667 S | 6/2015 | McCormack et al. |
| 9,186,193 B2 | 11/2015 | Kleiner et al. |
| D745,156 S | 12/2015 | McCormack et al. |
| 9,211,198 B2 | 12/2015 | Michelson |
| 9,220,608 B2 | 12/2015 | McKay |
| D750,249 S | 2/2016 | Grimberg, Jr. et al. |
| 9,271,765 B2 | 3/2016 | Blain |
| 9,333,086 B2 | 5/2016 | McCormack et al. |
| 9,358,127 B2 | 6/2016 | Duffield et al. |
| 9,381,049 B2 | 7/2016 | McCormack et al. |
| 9,427,264 B2 | 8/2016 | Kleiner et al. |
| 9,504,583 B2 | 11/2016 | Blain |
| 9,622,791 B2 | 4/2017 | McCormack et al. |
| 9,622,873 B2 | 4/2017 | McCormack et al. |
| 9,622,874 B2 | 4/2017 | McCormack et al. |
| 9,629,665 B2 | 4/2017 | McCormack et al. |
| 9,717,403 B2 | 8/2017 | Kleiner et al. |
| 9,937,053 B2 | 4/2018 | Melkent et al. |
| 10,039,649 B2 | 8/2018 | McCormack et al. |
| 10,149,673 B2 | 12/2018 | McCormack et al. |
| 10,172,721 B2 | 1/2019 | McCormack et al. |
| D841,165 S | 2/2019 | McCormack et al. |
| D841,167 S | 2/2019 | Ricca et al. |
| 10,201,375 B2 | 2/2019 | McCormack et al. |
| 10,206,787 B2 | 2/2019 | Voellmicke |
| 10,219,910 B2 | 3/2019 | McCormack et al. |
| 10,226,285 B2 | 3/2019 | McCormack et al. |
| 10,238,501 B2 | 3/2019 | McCormack et al. |
| 10,327,913 B2 | 6/2019 | Palmatier et al. |
| 10,456,175 B2 | 10/2019 | McCormack et al. |
| 10,568,666 B2 | 2/2020 | McCormack et al. |
| 10,588,672 B2 | 3/2020 | McCormack et al. |
| D884,895 S | 5/2020 | McCormack et al. |
| D887,552 S | 6/2020 | Tanaka et al. |
| 10,682,243 B2 | 6/2020 | Phan et al. |
| D911,525 S | 2/2021 | Tanaka et al. |
| RE48,501 E | 4/2021 | McCormack et al. |
| 11,272,964 B2 | 3/2022 | Mccormack et al. |
| 11,285,010 B2 | 3/2022 | Mccormack |
| 2001/0004710 A1 | 6/2001 | Felt et al. |
| 2001/0047208 A1 | 11/2001 | Michelson |
| 2001/0053914 A1 | 12/2001 | Landry et al. |
| 2002/0026195 A1 | 2/2002 | Layne et al. |
| 2002/0068941 A1 | 6/2002 | Hanson et al. |
| 2002/0077641 A1 | 6/2002 | Michelson |
| 2002/0107519 A1 | 8/2002 | Dixon et al. |
| 2002/0143343 A1 | 10/2002 | Castro |
| 2002/0147496 A1 | 10/2002 | Belef et al. |
| 2002/0165612 A1* | 11/2002 | Gerber ............. A61B 17/1671 623/17.11 |
| 2002/0169471 A1 | 11/2002 | Ferdinand |
| 2002/0177866 A1 | 11/2002 | Weikel et al. |
| 2003/0023312 A1 | 1/2003 | Thalgott |
| 2003/0028251 A1 | 2/2003 | Mathews |
| 2003/0032962 A1 | 2/2003 | McGahan et al. |
| 2003/0033017 A1 | 2/2003 | Lotz et al. |
| 2003/0083668 A1 | 5/2003 | Rogers et al. |
| 2003/0105526 A1 | 6/2003 | Bryant et al. |
| 2003/0109928 A1 | 6/2003 | Pasquet et al. |
| 2003/0139816 A1 | 7/2003 | Michelson |
| 2003/0144737 A1 | 7/2003 | Sherman |
| 2003/0149438 A1 | 8/2003 | Nichols et al. |
| 2003/0158553 A1 | 8/2003 | Michelson |
| 2003/0225416 A1 | 12/2003 | Bonvallet et al. |
| 2004/0010259 A1 | 1/2004 | Keller et al. |
| 2004/0059337 A1 | 3/2004 | Hanson et al. |
| 2004/0073217 A1 | 4/2004 | Michelson |
| 2004/0087948 A1 | 5/2004 | Suddaby |
| 2004/0087956 A1 | 5/2004 | Weikel et al. |
| 2004/0106999 A1 | 6/2004 | Mathews |
| 2004/0133277 A1 | 7/2004 | Michelson |
| 2004/0133280 A1 | 7/2004 | Trieu |
| 2004/0162562 A1 | 8/2004 | Martz |
| 2004/0215344 A1 | 10/2004 | Hochshculer et al. |
| 2005/0010294 A1 | 1/2005 | Michelson |
| 2005/0015097 A1 | 1/2005 | Mujwid et al. |
| 2005/0015149 A1 | 1/2005 | Michelson |
| 2005/0021042 A1 | 1/2005 | Marnay et al. |
| 2005/0027358 A1 | 2/2005 | Suddaby |
| 2005/0033432 A1 | 2/2005 | Gordon et al. |
| 2005/0038511 A1 | 2/2005 | Martz et al. |
| 2005/0049623 A1 | 3/2005 | Moore et al. |
| 2005/0049705 A1 | 3/2005 | Hale et al. |
| 2005/0055096 A1 | 3/2005 | Serhan et al. |
| 2005/0065518 A1 | 3/2005 | Michelson |
| 2005/0065519 A1 | 3/2005 | Michelson |
| 2005/0065608 A1 | 3/2005 | Michelson |
| 2005/0065609 A1 | 3/2005 | Wardlaw |
| 2005/0080422 A1 | 4/2005 | Otte et al. |
| 2005/0090829 A1 | 4/2005 | Martz et al. |
| 2005/0090901 A1 | 4/2005 | Studer |
| 2005/0113842 A1 | 5/2005 | Bertagnoli et al. |
| 2005/0119680 A1 | 6/2005 | Dykes |
| 2005/0124993 A1 | 6/2005 | Chappuis |
| 2005/0149192 A1 | 7/2005 | Zucherman et al. |
| 2005/0159650 A1 | 7/2005 | Raymond et al. |
| 2005/0159746 A1 | 7/2005 | Grob et al. |
| 2005/0177240 A1 | 8/2005 | Blain |
| 2005/0182417 A1 | 8/2005 | Pagano |
| 2005/0209698 A1 | 9/2005 | Gordon et al. |
| 2005/0216018 A1 | 9/2005 | Sennett |
| 2005/0234455 A1 | 10/2005 | Binder et al. |
| 2005/0240188 A1 | 10/2005 | Chow et al. |
| 2005/0251146 A1 | 11/2005 | Martz et al. |
| 2005/0251257 A1 | 11/2005 | Mitchell et al. |
| 2005/0267480 A1 | 12/2005 | Suddaby |
| 2006/0004367 A1 | 1/2006 | Alamin et al. |
| 2006/0015184 A1 | 1/2006 | Winterbottom et al. |
| 2006/0036243 A1 | 2/2006 | Sasso et al. |
| 2006/0036247 A1 | 2/2006 | Michelson |
| 2006/0036323 A1 | 2/2006 | Carl et al. |
| 2006/0041311 A1 | 2/2006 | McLeer |
| 2006/0058790 A1 | 3/2006 | Carl et al. |
| 2006/0058793 A1 | 3/2006 | Michelson |
| 2006/0058878 A1 | 3/2006 | Michelson |
| 2006/0069442 A1 | 3/2006 | Michelson |
| 2006/0079905 A1 | 4/2006 | Beyar et al. |
| 2006/0079962 A1 | 4/2006 | Michelson |
| 2006/0085068 A1 | 4/2006 | Barry |
| 2006/0085074 A1 | 4/2006 | Raiszadeh |
| 2006/0095028 A1 | 5/2006 | Bleich |
| 2006/0095036 A1 | 5/2006 | Hammerslag |
| 2006/0111779 A1 | 5/2006 | Peterson |
| 2006/0111780 A1 | 5/2006 | Petersen |

(56) References Cited

U.S. PATENT DOCUMENTS

| | | |
|---|---|---|
| 2006/0111781 A1 | 5/2006 | Petersen |
| 2006/0142762 A1 | 6/2006 | Michelson |
| 2006/0149279 A1 | 7/2006 | Mathews |
| 2006/0149289 A1 | 7/2006 | Winslow et al. |
| 2006/0184172 A1 | 8/2006 | Michelson |
| 2006/0189991 A1 | 8/2006 | Bickley |
| 2006/0190081 A1 | 8/2006 | Kraus et al. |
| 2006/0195109 A1 | 8/2006 | McGahan et al. |
| 2006/0200137 A1 | 9/2006 | Soboleski et al. |
| 2006/0200138 A1 | 9/2006 | Michelson |
| 2006/0200139 A1 | 9/2006 | Michelson |
| 2006/0206118 A1 | 9/2006 | Kim et al. |
| 2006/0217812 A1 | 9/2006 | Lambrecht et al. |
| 2006/0229627 A1 | 10/2006 | Hunt et al. |
| 2006/0235391 A1 | 10/2006 | Sutterlin |
| 2006/0241597 A1 | 10/2006 | Mitchell et al. |
| 2006/0241626 A1 | 10/2006 | McGahan et al. |
| 2006/0241758 A1 | 10/2006 | Peterman et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0259142 A1 | 11/2006 | Dooris et al. |
| 2006/0271195 A1 | 11/2006 | Thramann |
| 2006/0276790 A1 | 12/2006 | Dawson et al. |
| 2006/0276801 A1 | 12/2006 | Yerby et al. |
| 2006/0276897 A1 | 12/2006 | Winslow et al. |
| 2006/0293663 A1 | 12/2006 | Walkenhorst et al. |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0032871 A1 | 2/2007 | Michelson |
| 2007/0043362 A1 | 2/2007 | Malandain et al. |
| 2007/0050031 A1 | 3/2007 | Khosrowshahi |
| 2007/0055245 A1 | 3/2007 | Sasso et al. |
| 2007/0055263 A1 | 3/2007 | Way et al. |
| 2007/0073402 A1 | 3/2007 | Vresilovic et al. |
| 2007/0083265 A1 | 4/2007 | Malone |
| 2007/0123863 A1 | 5/2007 | Winslow et al. |
| 2007/0123888 A1 | 5/2007 | Bleich et al. |
| 2007/0135814 A1 | 6/2007 | Farris |
| 2007/0135921 A1 | 6/2007 | Park |
| 2007/0149976 A1 | 6/2007 | Hale et al. |
| 2007/0149983 A1 | 6/2007 | Link |
| 2007/0150061 A1 | 6/2007 | Trieu |
| 2007/0161991 A1 | 7/2007 | Altarac et al. |
| 2007/0162138 A1 | 7/2007 | Heinz |
| 2007/0179617 A1 | 8/2007 | Brown et al. |
| 2007/0179619 A1 | 8/2007 | Grob et al. |
| 2007/0191861 A1 | 8/2007 | Allard et al. |
| 2007/0225721 A1 | 9/2007 | Thelen et al. |
| 2007/0225812 A1 | 9/2007 | Gill |
| 2007/0244483 A9 | 10/2007 | Winslow et al. |
| 2007/0250167 A1 | 10/2007 | Bray et al. |
| 2007/0276491 A1 | 11/2007 | Ahrens |
| 2007/0282441 A1 | 12/2007 | Stream et al. |
| 2007/0288014 A1 | 12/2007 | Shadduck et al. |
| 2007/0293949 A1 | 12/2007 | Salerni et al. |
| 2007/0299451 A1 | 12/2007 | Tulkis |
| 2008/0015581 A1 | 1/2008 | Eckman |
| 2008/0021457 A1 | 1/2008 | Anderson et al. |
| 2008/0021464 A1 | 1/2008 | Morin et al. |
| 2008/0058954 A1 | 3/2008 | Trieu |
| 2008/0065219 A1 | 3/2008 | Dye |
| 2008/0077245 A1 | 3/2008 | Lee |
| 2008/0097436 A1 | 4/2008 | Culbert et al. |
| 2008/0108996 A1 | 5/2008 | Padget et al. |
| 2008/0140207 A1 | 6/2008 | Olmos et al. |
| 2008/0154377 A1 | 6/2008 | Voellmicke |
| 2008/0161810 A1 | 7/2008 | Melkent |
| 2008/0161929 A1 | 7/2008 | McCormack et al. |
| 2008/0167657 A1 | 7/2008 | Greenhalgh |
| 2008/0177311 A1 | 7/2008 | Winslow et al. |
| 2008/0183209 A1 | 7/2008 | Robinson et al. |
| 2008/0195206 A1 | 8/2008 | Chee et al. |
| 2008/0208341 A1 | 8/2008 | McCormack et al. |
| 2008/0216846 A1 | 9/2008 | Levin |
| 2008/0234677 A1 | 9/2008 | Dahners et al. |
| 2008/0234758 A1 | 9/2008 | Fisher et al. |
| 2008/0249571 A1 | 10/2008 | Sasso et al. |
| 2008/0255564 A1 | 10/2008 | Michelson |
| 2008/0255618 A1 | 10/2008 | Fisher et al. |
| 2008/0255622 A1 | 10/2008 | Mickiewicz et al. |
| 2008/0255666 A1 | 10/2008 | Fisher et al. |
| 2008/0255667 A1 | 10/2008 | Horton |
| 2008/0275455 A1 | 11/2008 | Berry et al. |
| 2008/0287955 A1 | 11/2008 | Michelson |
| 2008/0300685 A1 | 12/2008 | Carls et al. |
| 2008/0306537 A1 | 12/2008 | Culbert |
| 2008/0312744 A1 | 12/2008 | Vresilovic et al. |
| 2009/0131986 A1 | 5/2009 | Lee et al. |
| 2009/0138053 A1 | 5/2009 | Assell et al. |
| 2009/0177205 A1 | 7/2009 | McCormack et al. |
| 2009/0177215 A1 | 7/2009 | Stack et al. |
| 2009/0177237 A1 | 7/2009 | Zucherman et al. |
| 2009/0182429 A1 | 7/2009 | Humphreys et al. |
| 2009/0234397 A1 | 9/2009 | Petersen |
| 2009/0248076 A1 | 10/2009 | Reynolds et al. |
| 2009/0263461 A1 | 10/2009 | McKay |
| 2009/0270929 A1 | 10/2009 | Suddaby et al. |
| 2009/0275994 A1 | 11/2009 | Phan et al. |
| 2009/0297603 A1 | 12/2009 | Joshi |
| 2009/0306671 A1 | 12/2009 | McCormack et al. |
| 2009/0312763 A1 | 12/2009 | McCormack et al. |
| 2010/0036418 A1 | 2/2010 | Siemionow et al. |
| 2010/0069912 A1 | 3/2010 | McCormack et al. |
| 2010/0082065 A1 | 4/2010 | Butler et al. |
| 2010/0086185 A1 | 4/2010 | Weiss |
| 2010/0093829 A1 | 4/2010 | Gorman |
| 2010/0111829 A1 | 5/2010 | Drapeau et al. |
| 2010/0114318 A1 | 5/2010 | Gittings et al. |
| 2010/0145391 A1 | 6/2010 | Kleiner |
| 2010/0145459 A1 | 6/2010 | Mcdonough et al. |
| 2010/0191241 A1 | 7/2010 | McCormack et al. |
| 2010/0211104 A1 | 8/2010 | Moumene et al. |
| 2010/0286783 A1 | 11/2010 | Lechmann et al. |
| 2011/0004247 A1 | 1/2011 | Lechmann et al. |
| 2011/0022089 A1 | 1/2011 | Assell et al. |
| 2011/0054613 A1 | 3/2011 | Hansen |
| 2011/0077686 A1 | 3/2011 | Mishra et al. |
| 2011/0082548 A1 | 4/2011 | Assell et al. |
| 2011/0144755 A1 | 6/2011 | Baynham et al. |
| 2011/0184470 A1 | 7/2011 | Gorek et al. |
| 2011/0190821 A1 | 8/2011 | Chin et al. |
| 2011/0245930 A1 | 10/2011 | Alley et al. |
| 2011/0295327 A1 | 12/2011 | Moskowitz et al. |
| 2011/0307061 A1 | 12/2011 | Assell et al. |
| 2012/0010659 A1 | 1/2012 | Angert et al. |
| 2012/0010662 A1 | 1/2012 | O'Neil et al. |
| 2012/0010669 A1 | 1/2012 | O'Neil et al. |
| 2012/0029545 A1 | 2/2012 | Nelson et al. |
| 2012/0065613 A1 | 3/2012 | Pepper et al. |
| 2012/0130496 A1 | 5/2012 | Duffield et al. |
| 2012/0143334 A1 | 6/2012 | Boyce et al. |
| 2012/0179259 A1 | 7/2012 | Mcdonough et al. |
| 2012/0215259 A1 | 8/2012 | Cannestra |
| 2012/0245689 A1 | 9/2012 | Gimbel et al. |
| 2012/0265250 A1 | 10/2012 | Ali |
| 2012/0277801 A1 | 11/2012 | Marik et al. |
| 2012/0283776 A1 | 11/2012 | Mishra |
| 2012/0323242 A1 | 12/2012 | Tsuang et al. |
| 2013/0006364 A1 | 1/2013 | McCormack et al. |
| 2013/0012994 A1 | 1/2013 | McCormack et al. |
| 2013/0013070 A1 | 1/2013 | McCormack et al. |
| 2013/0018474 A1 | 1/2013 | McCormack et al. |
| 2013/0023889 A1 | 1/2013 | Blain et al. |
| 2013/0023995 A1 | 1/2013 | McCormack et al. |
| 2013/0023996 A1 | 1/2013 | McCormack et al. |
| 2013/0030440 A1 | 1/2013 | McCormack et al. |
| 2013/0030532 A1 | 1/2013 | McCormack et al. |
| 2013/0110168 A1 | 5/2013 | McCormack et al. |
| 2013/0110243 A1 | 5/2013 | Patterson et al. |
| 2013/0123922 A1 | 5/2013 | McCormack |
| 2013/0144389 A1 | 6/2013 | Bonutti |
| 2013/0226239 A1 | 8/2013 | Altarac et al. |

(56) References Cited

U.S. PATENT DOCUMENTS

| | | |
|---|---|---|
| 2013/0238095 A1 | 9/2013 | Pavento et al. |
| 2013/0253649 A1 | 9/2013 | Davis |
| 2013/0274763 A1 | 10/2013 | Drapeau et al. |
| 2013/0310839 A1 | 11/2013 | McCormack et al. |
| 2013/0310878 A1 | 11/2013 | McCormack et al. |
| 2013/0310943 A1 | 11/2013 | McCormack et al. |
| 2013/0317548 A1 | 11/2013 | Malone |
| 2013/0338720 A1 | 12/2013 | Kleiner |
| 2014/0012318 A1 | 1/2014 | Goel |
| 2014/0025113 A1 | 1/2014 | McCormack et al. |
| 2014/0100657 A1 | 4/2014 | McCormack et al. |
| 2014/0114415 A1 | 4/2014 | Tyber |
| 2014/0135930 A1 | 5/2014 | Georges |
| 2014/0172103 A1 | 6/2014 | O'Neil et al. |
| 2014/0228959 A1 | 8/2014 | Niemiec et al. |
| 2014/0296916 A1 | 10/2014 | Mccormack et al. |
| 2014/0379087 A1 | 12/2014 | McCormack |
| 2015/0025635 A1 | 1/2015 | Laubert |
| 2015/0100129 A1 | 4/2015 | Waugh et al. |
| 2015/0201977 A1 | 7/2015 | Mccormack et al. |
| 2015/0230834 A1 | 8/2015 | Cannestra |
| 2015/0297357 A1 | 10/2015 | McCormack et al. |
| 2015/0328005 A1 | 11/2015 | Padovani et al. |
| 2015/0328010 A1 | 11/2015 | Martynova et al. |
| 2015/0342648 A1 | 12/2015 | Mccormack et al. |
| 2015/0342649 A1 | 12/2015 | Mccormack et al. |
| 2016/0008040 A1 | 1/2016 | Mccormack et al. |
| 2016/0242754 A1 | 8/2016 | Mccormack et al. |
| 2016/0250035 A1 | 9/2016 | De Villiers et al. |
| 2016/0317316 A1 | 11/2016 | Mccormack et al. |
| 2016/0331553 A1 | 11/2016 | Liou et al. |
| 2017/0027713 A1 | 2/2017 | Kleiner |
| 2017/0135733 A1 | 5/2017 | Donner et al. |
| 2017/0189199 A1 | 7/2017 | Maier et al. |
| 2017/0216044 A1 | 8/2017 | McCormack et al. |
| 2017/0281360 A1 | 10/2017 | Seifert |
| 2017/0348027 A1 | 12/2017 | McCormack et al. |
| 2017/0354444 A1 | 12/2017 | McCormack et al. |
| 2017/0360571 A1 | 12/2017 | Mesiwala |
| 2018/0161077 A1 | 6/2018 | McCormack et al. |
| 2018/0303631 A1 | 10/2018 | Phan et al. |
| 2019/0083271 A1 | 3/2019 | Donner et al. |
| 2019/0209151 A1 | 7/2019 | McCormack et al. |
| 2019/0239932 A1 | 8/2019 | McCormack et al. |
| 2019/0240041 A1 | 8/2019 | McCormack et al. |
| 2019/0247099 A1 | 8/2019 | McCormack et al. |
| 2019/0307571 A1 | 10/2019 | McCormack et al. |
| 2019/0307572 A1 | 10/2019 | McCormack et al. |
| 2019/0350626 A1 | 11/2019 | McCormack et al. |
| 2020/0085475 A1 | 3/2020 | McCormack et al. |
| 2020/0155205 A1 | 5/2020 | Tanaka et al. |
| 2020/0289285 A1 | 9/2020 | Siemionow et al. |
| 2020/0375633 A1 | 12/2020 | McCormack et al. |
| 2020/0405502 A1 | 12/2020 | Gephart et al. |
| 2021/0059833 A1 | 3/2021 | Tanaka et al. |
| 2021/0378720 A1 | 12/2021 | Mccormack et al. |
| 2021/0386434 A1 | 12/2021 | Tanaka et al. |
| 2022/0031297 A1 | 2/2022 | Mccormack et al. |
| 2022/0151663 A1 | 5/2022 | Mccormack et al. |
| 2022/0211513 A1 | 7/2022 | Mccormack et al. |

FOREIGN PATENT DOCUMENTS

| | | |
|---|---|---|
| JP | H11508781 A | 8/1999 |
| JP | 2004523288 A | 8/2004 |
| JP | 2008509735 A | 4/2008 |
| JP | 2008522787 A | 7/2008 |
| JP | 2012501234 A | 1/2012 |
| JP | 2014516268 A | 7/2014 |
| WO | 9641582 A1 | 12/1996 |
| WO | 99/49818 A1 | 10/1999 |
| WO | 00/035388 A1 | 6/2000 |
| WO | 00/53126 A1 | 9/2000 |
| WO | 01/01895 A1 | 1/2001 |
| WO | 02/34120 A2 | 5/2002 |
| WO | 02/038062 A2 | 5/2002 |
| WO | 02/076335 A2 | 10/2002 |
| WO | 2005032358 A2 | 4/2005 |
| WO | 2006058221 A2 | 6/2006 |
| WO | 2006130791 A2 | 12/2006 |
| WO | 2007120903 A2 | 10/2007 |
| WO | 2008083349 A1 | 7/2008 |
| WO | 2008127978 A2 | 10/2008 |
| WO | 2008153732 A1 | 12/2008 |
| WO | 2009089367 A2 | 7/2009 |
| WO | 2009148619 A2 | 12/2009 |
| WO | 2010030994 A2 | 3/2010 |
| WO | 2010074714 A2 | 7/2010 |
| WO | 2010107692 A1 | 9/2010 |
| WO | 2011050140 A1 | 4/2011 |
| WO | 2013043584 A2 | 3/2013 |
| WO | 2014188280 A2 | 11/2014 |
| WO | 2016049784 A1 | 4/2016 |

OTHER PUBLICATIONS

Spinal News International, "FDA clears Renovis Surgical 3D-printed titanium standalone cervical cage", first available Apr. 11, 2016. https://spinalnewsinternational.com/fda-clears-renovis-surgical-3d-printed-titanium-standalone-cervical-cage/.

Research Gate, "DTRAX Posterior Cervical Cage", first available Jul. 2016. (hllps://www.researchgate.net/figure/ DTRAX-Posterior-Cervical-Cage-Note-The-cervical-cages-are-manufactured-from-implant_fig3_305314436).

Providence Medical Technology, "Cavux Cervical Cages", first available Oct. 5, 2016. (hllps://web.archive.org/web/20161005063842/https:/providencemt.com/cavux-cervical-cages/).

Providence Medical Technology, "Posterior Cervical Stabilization System (PCSS)", first available Jun. 21, 2020. (hllps://web.archive.org/web/20200621181620/hllps:/providencemt.com/pcss/).

Atul Goel, Facetai distraction as treatment for single- and multilevel cervical spondylotic radiculopathy and myelopathy: a preliminary report, J Neurosurg Spine, Jun. 2011, pp. 689-696.

Press Release, Interventional Spine, Inc., Interventional Spine, Inc. Introduces the PERPOS Fusion Facet Prep Kit, Oct. 14, 2008, 1 Page.

Press Release, minSURG Corp., Orthopedic Development Corporation's TruFUSE Procedure Tops 1,750 Patients in First Year, Sep. 24, 2007, 1 Page.

Press Release, Interventional Spine, Inc., FDA Grants Conditional Approval to Interventional Spine's PercuDyn System IDE Application, Jul. 1, 2008, 1 Page.

Stein, et al., "Percutaneous Facet Joint Fusion: Preliminary Experience," Journal of Vascular and Interventional Radiology, Jan.-Feb. 1993, pp. 69-74, vol. 4, No. 1.

\* cited by examiner

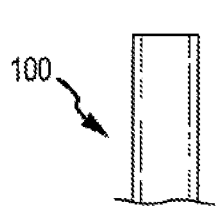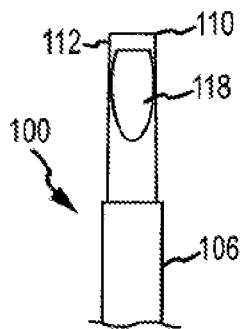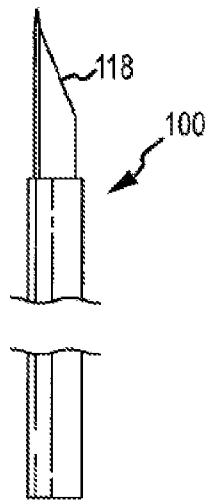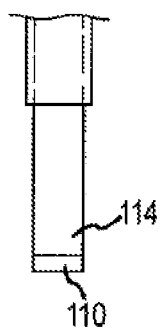
FIG.3A  FIG.3B  FIG.3C
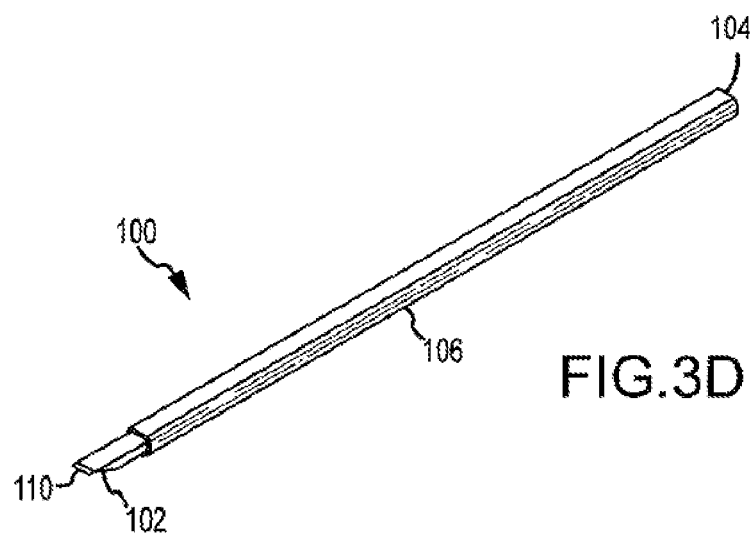
FIG.3D

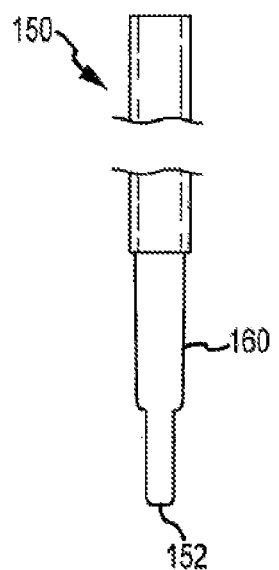
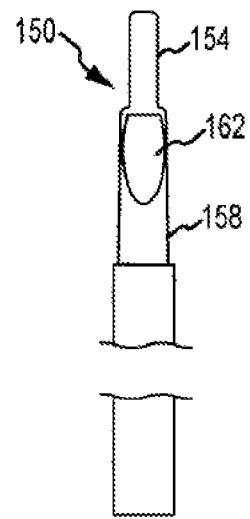
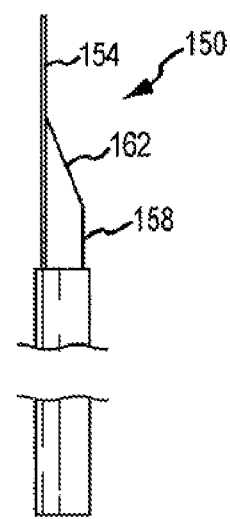
FIG.8A  FIG.8B  FIG.8C
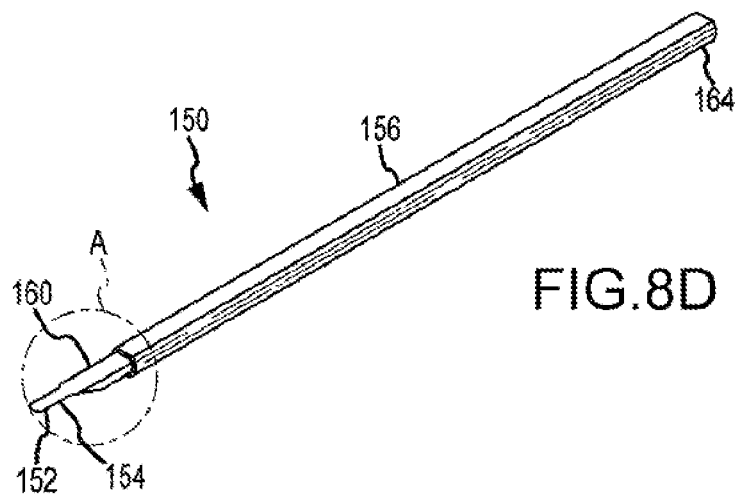
FIG.8D

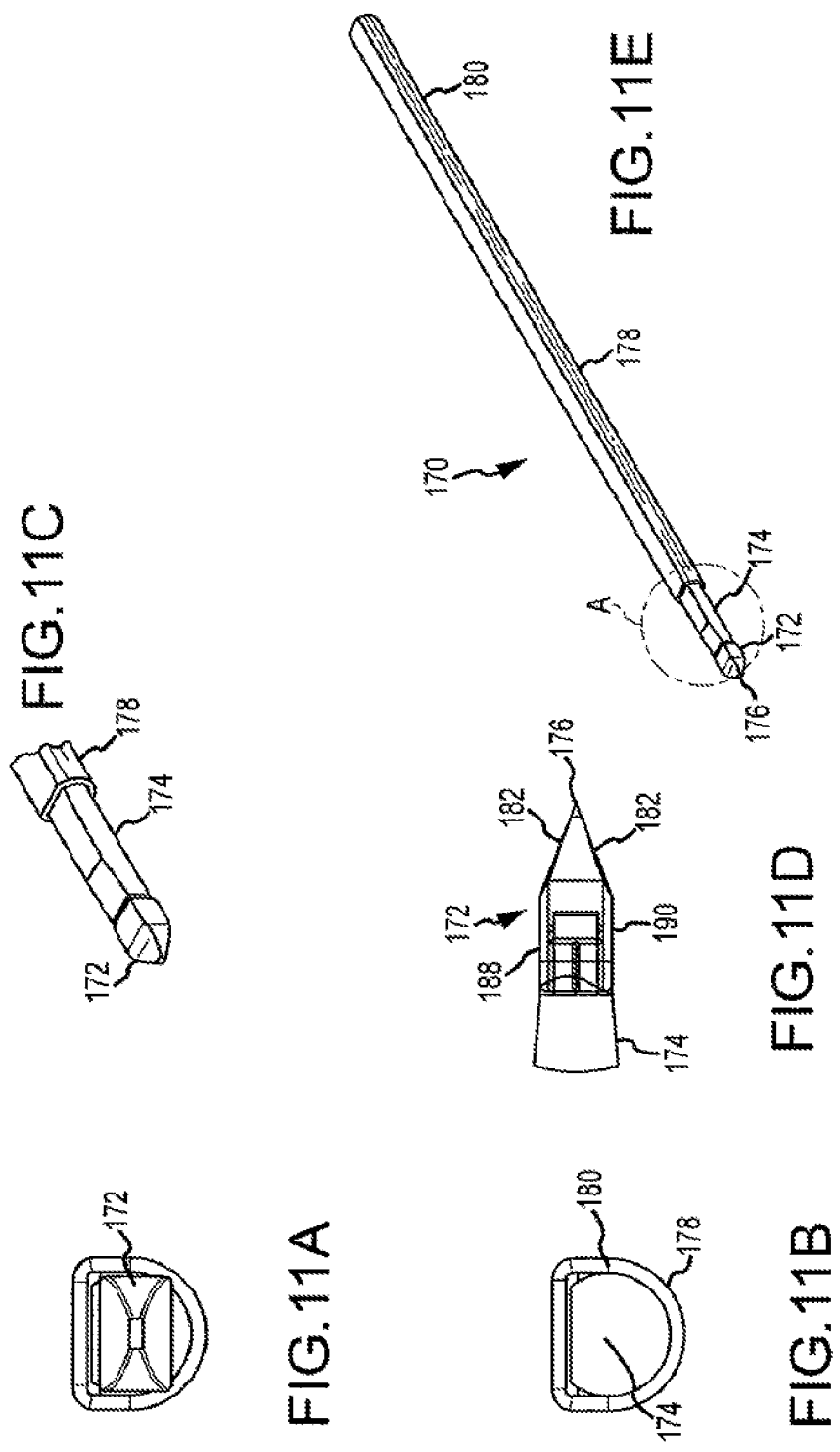

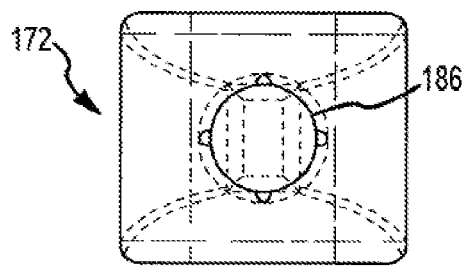
FIG.12A
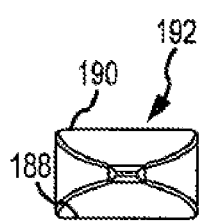 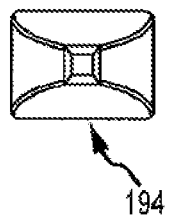 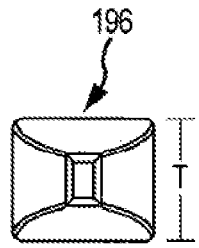
FIG.12B  FIG.12C  FIG.12D
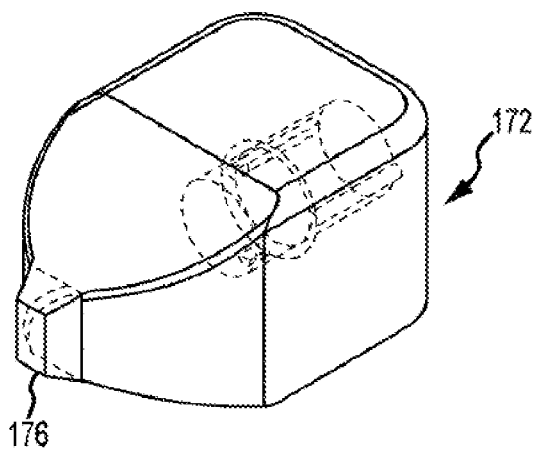
FIG.12E

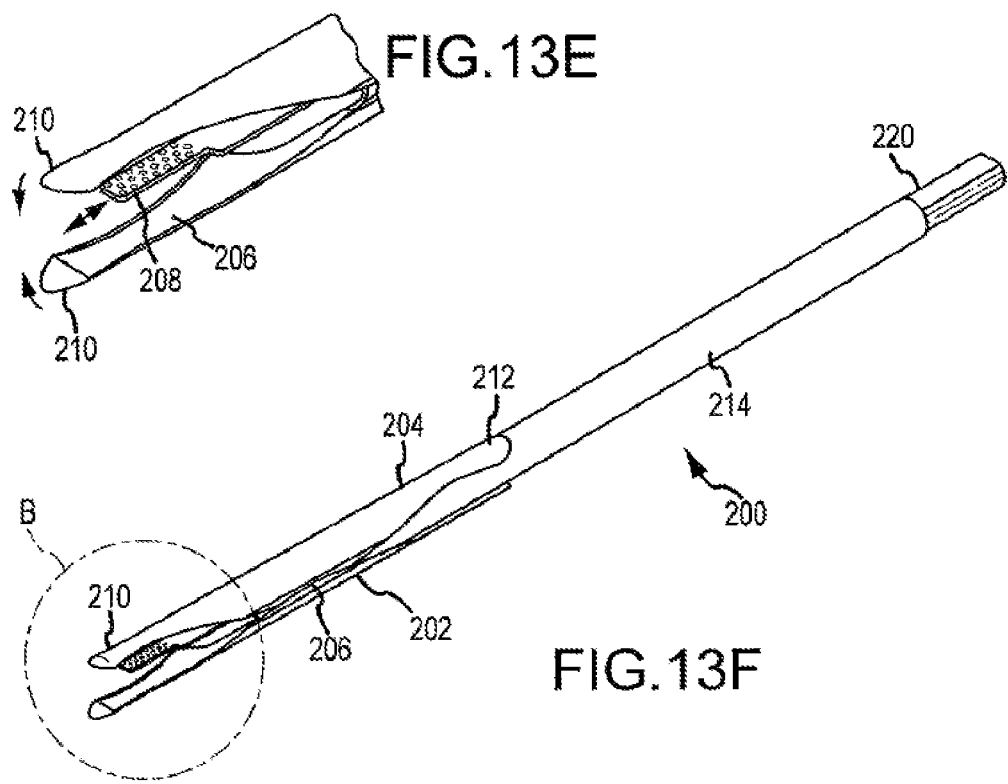
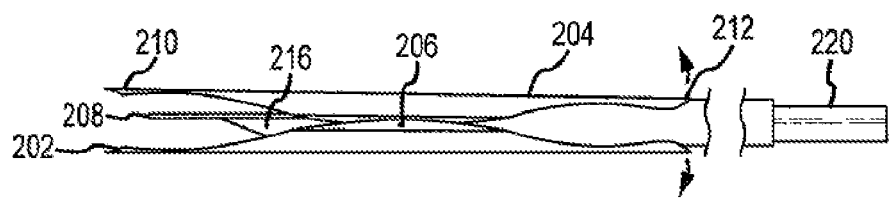

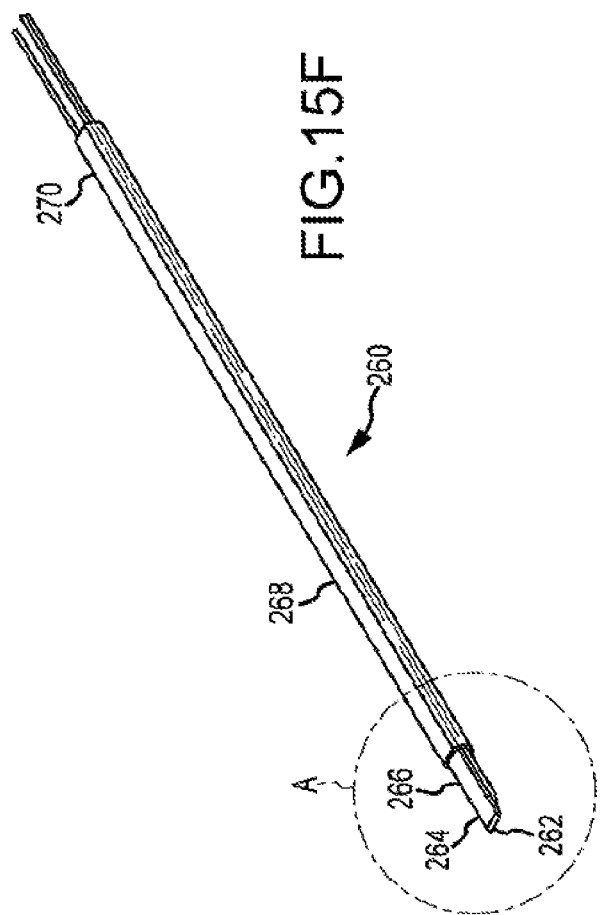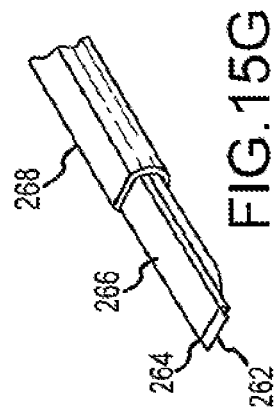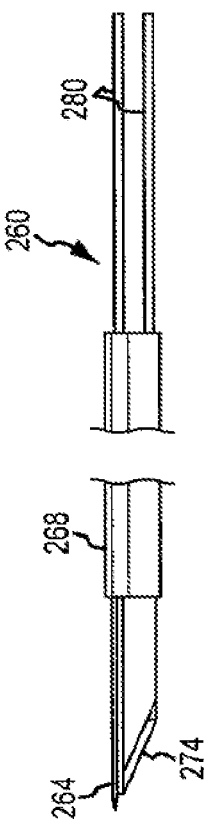

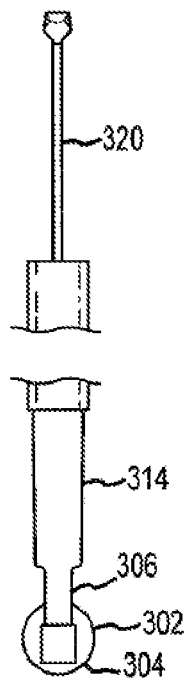
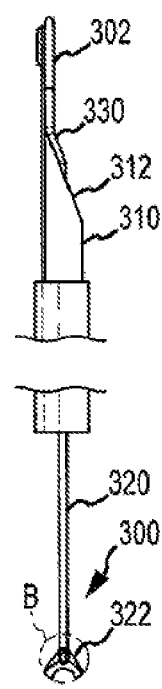
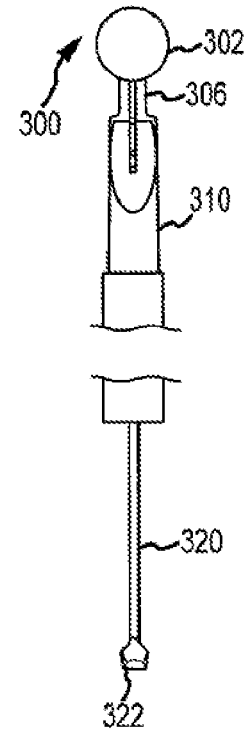
FIG.16A  FIG.16B  FIG.16C
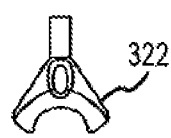
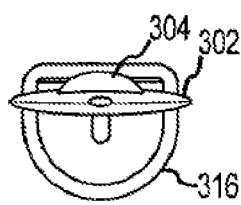
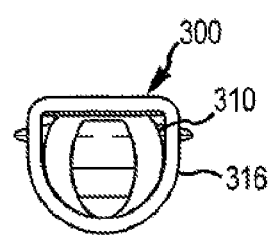
FIG.16D  FIG.16E  FIG.16F

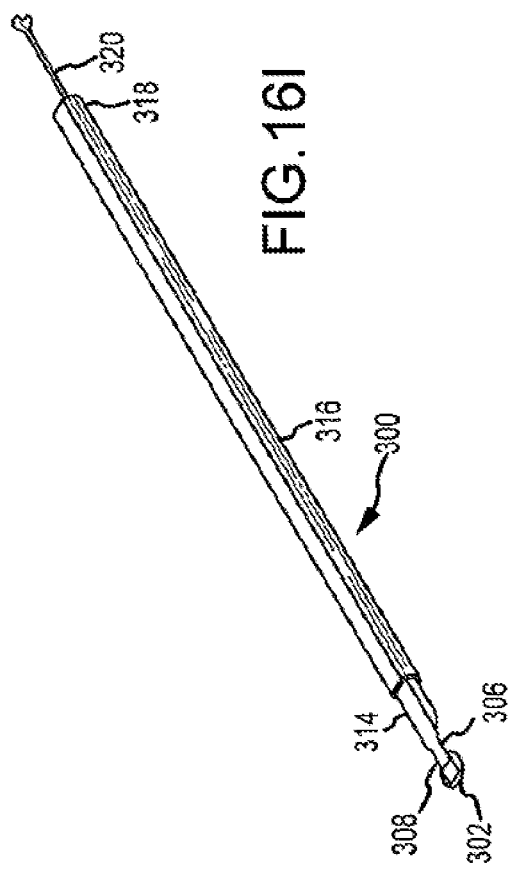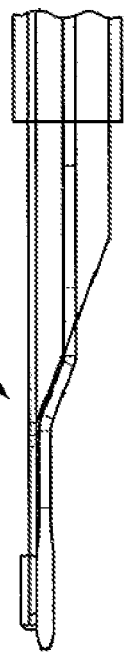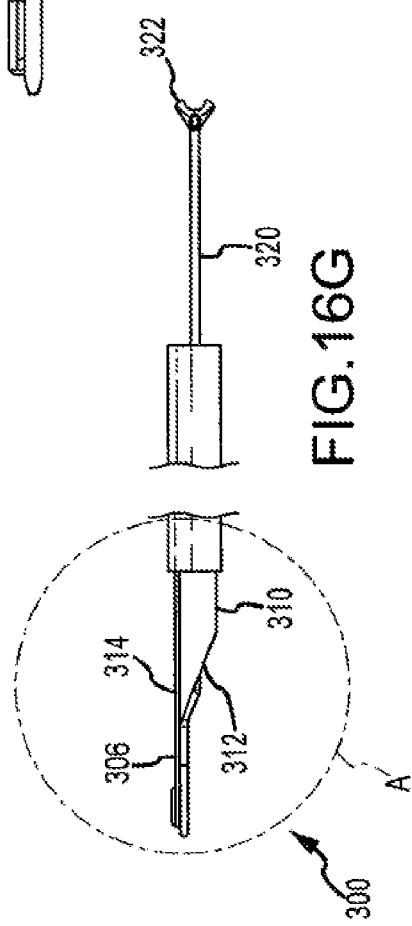

METHODS AND APPARATUS FOR ACCESSING AND TREATING THE FACET JOINT

CROSS REFERENCE TO RELATED APPLICATIONS

This application is a continuation application of Ser. No. 15/467,773, filed Mar. 23, 2017, which is a continuation application of Ser. No. 14/675,626, filed Mar. 31, 2015, which is a continuation application of Ser. No. 12/350,609, filed Jan. 8, 2009, now U.S. Pat. No. 9,005,288, which claims priority to U.S. Provisional Patent Application No. 61/020,082, entitled "METHODS AND APPARATUS FOR ACCESSING AND TREATING THE FACET JOINT," filed on Jan. 9, 2008. The full disclosures of the above-listed patent applications are hereby incorporated by reference herein.

FIELD

This invention pertains generally to treatment of the facet joint, and more particularly to tools and methods for accessing, preparing and facilitating spinal distraction.

BACKGROUND OF THE INVENTION

Neck and arm pain is a common ailment of the aging spine due to disc herniations, facet arthropathy and thickening of spinal ligaments which narrow spinal canal dimensions. This results in compression of the spinal cord or nerve roots, or both. Radicular pain is typically due to disc herniation and foraminal narrowing, which compresses the cervical nerve roots and causes radicular pain. Extension and ipsilateral rotation of the neck further reduces the foraminal area and contributes to pain, nerve root compression, and neural injury. Neck flexion generally increases the foraminal area.

Cervical disc herniations and foraminal stenosis typically present with upper extremity radicular pain without major motor or sensory neurologic deficit. A well-described treatment for cervical disc herniations is closed traction. There are a number of marketed devices that alleviate pain by pulling on the head to increase foraminal height.

Cervical disc herniations have been treated with anterior and posterior surgery. The vast majority are performed through an anterior surgical approach, which entails a spinal fusion. These surgeries are expensive and beget additional surgeries due to change in biomechanics of the neck. There is a 3% incidence of re-operation per year that is cumulative at adjacent levels.

There is a need in the art for minimally invasive methods and devices for accessing and preparing and distracting the facet joint to increase foraminal height and reduce radicular symptoms for patients with soft and hard disc disease.

BRIEF SUMMARY OF THE INVENTION

Devices and techniques are disclosed for a percutaneous or minimally invasive surgical implantation to reduce radicular symptoms by inserting an expandable cervical distraction implant in the facet joint at a symptomatic level to decompress the nerve tissue and preserve motion. In particular, embodiments of the present invention provide for accessing and distracting the cervical facet to increase the foraminal dimension. In one embodiment, the implant of the present invention, when positioned in the cervical facet joint, increases the space between the articular facets, to increase the foraminal area or dimension, and reduce pressure on the nerve and associated blood vessels.

The procedure may be performed under conscious sedation in order to obtain intra-operative patient symptom feedback.

An aspect of an embodiment of the invention is an apparatus for accessing an interior region of a facet joint, comprising an elongate handle having a proximal end and a distal end, and a blade disposed at the distal end of the handle. The blade may have a flat leading edge such that placement of the blade through the facet capsule and into the facet cavity to generate a slit-shaped aperture in the facet capsule. Preferably, the aperture may extend substantially parallel to the first and second articulating subchondral surfaces.

In one embodiment, the blade comprises a planar lower surface extending from the leading edge, and extending proximally away from the leading edge, wherein the planar surface provides a platform to guide a second instrument through the aperture for treatment of the facet joint.

In one mode of the current embodiment, the blade comprises an upper surface opposite the lower surface, with the upper surface and lower surface defining a thickness, generally sized to be smaller than the distance between the first and second boundaries of a facet cavity.

Preferably, in one embodiment, a beveled surface emanates from the upper blade surface and extends proximally away from the leading edge. Accordingly, the thickness increases proximally along the beveled surface. The beveled surface generally facilitates manipulation of the blade into the cavity.

In one embodiment, the handle comprises a shaft extending from the distal end to the proximal end, wherein the shaft comprises a beveled surface emanating at or near the leading edge and extending proximally away from the leading edge. The beveled surface facilitates insertion of the blade into the cavity at an angle not aligned with the first and second cavity boundaries.

In another embodiment, the shaft is disposed within a central channel running along the length of the handle, and extends from the distal end of the handle. The shaft may have a D-shaped cross section providing a flat planar surface in cooperation with the blade.

Another aspect of an embodiment is an apparatus for decorticating an interior region of a facet joint, comprising an elongate handle having a proximal end and a distal end, and a rasp configured to decorticate a at least one of the articulating subchondral surfaces. The rasp may have a roughened planar surface extending distally outward from the distal end of the handle, and may be generally spatula-shaped and sized to be delivered into the facet joint via an aperture in the joint capsule and oriented in the joint substantially in line with the plane of the facet joint articulating surfaces. Generally the rasp comprises a compliant, thin cross section that allows the rasp to bend while being delivered into the facet from an angle out of alignment with the plane of the facet joint articulating surfaces.

The blade may have substantially planar lower surface extending from the leading edge, and extend proximally away from the leading edge. This planar surface may provide a platform for guiding the rasp in cooperation with a second instrument through the aperture for treatment of the facet joint.

In another embodiment, the rasp comprises an upper roughened surface opposite and substantially parallel with the lower surface, wherein the thickness is sized to be smaller than the distance between the first and second boundaries of a facet cavity, and to dispose the rasp to bending under light to moderate pressure. A beveled surface may emanate from the upper surface at a point proximal from a leading edge of the rasp and extending proximally away from the leading edge.

Another aspect of an embodiment is an apparatus for accessing an interior region of a facet joint, comprising an elongate handle having a proximal end and a distal end, and a spatula-shaped tip disposed at the distal end of the handle, with the tip comprising upper and lower parallel planar surface extending distally outward from the distal end of the handle. The tip may be sized to be delivered into the facet joint via an aperture in the joint capsule and oriented in the joint substantially in line with the plane of the facet joint articulating surfaces.

In one embodiment, the upper and lower parallel planar surfaces define a thickness that allows the tip to bend while being delivered into the facet from an angle out of alignment with the plane of the facet joint articulating surfaces.

In another embodiment, lower planar surface provides a platform for guiding a second instrument through the aperture for treatment of the facet joint.

The thickness may be generally sized to be smaller than the distance between the first and second boundaries of a facet cavity, and to dispose the tip to bending under light to moderate pressure. The apparatus may have a beveled surface emanating from the upper surface at a point proximal from a leading edge of the tip and extending proximally away from the leading edge.

In one embodiment, the handle comprises a shaft extending from the distal end to the proximal end, the shaft having a beveled surface emanating from the upper surface and terminating at a proximal location toward the handle. The lower planar surface may extend beyond the proximal location to create a platform for guiding a second instrument to the aperture and introducing the second instrument into the cavity.

The second instrument may comprise a rasp configured to decorticate at least one of the articulating surfaces, a distracter for distracting the articulating surfaces, an injector for delivering an agent into the cavity, or an introducer for delivering an implant into the cavity. The tip may function as a platform configured to receive an expandable implant and deliver the implant to a location within the cavity.

Another aspect of an embodiment is an apparatus for distracting two adjacent vertebrae, the being vertebrae separated by a facet joint comprising first and second articulating subchondral surfaces forming a facet cavity enclosed by a facet capsule. The apparatus may include an elongate handle having a proximal end and a distal end; and a wedge detachably disposed at the distal end of the handle. The wedge may have upper and lower beveled surfaces that converge toward a distal tip of the wedge, and is sized to be delivered into the cavity through an aperture in the capsule so that the upper and lower beveled surfaces contact the first and second articulating subchondral surfaces and distract the surfaces as the wedge is driven into the cavity.

In one embodiment, the wedge may comprise a recess on a proximal end of the wedge for detachably coupling the wedge to the handle.

In another embodiment, the apparatus may further include a shaft extending from the distal end of the handle proximal to the wedge. The wedge may be detachably coupled to the shaft. In one embodiment, the shaft may have a planar surface leading from the handle to the wedge to provide a platform for guiding the wedge in cooperation with a second instrument through the aperture.

Generally, the upper and lower beveled surfaces extend proximally from the distal tip to parallel upper and lower distraction surfaces, wherein the distraction surfaces are distanced from each other by a distraction thickness. The distraction thickness may correlate to a desired distraction of the articulating surfaces of the facet joint.

In another embodiment, wherein the wedge comprises one of a plurality of detachable wedges, with each of the detachable wedges having an increasingly larger distraction thickness such that the plurality of detachable wedges may be delivered to the facet joint in series from thinnest to thickest to incrementally distract the facet joint.

In a preferred embodiment, the upper and lower beveled surfaces converge to a nipple located at the distal end of the wedge, wherein the nipple is sized to be inserted in the cavity between the articulating surfaces.

Another aspect of an embodiment is an apparatus for distracting two adjacent vertebrae, having an elongate handle with a proximal end and a distal end, and upper and lower reciprocating members disposed at the distal end of the handle. The upper and lower reciprocating members may be coupled to the handle via a hinge located between proximal and distal ends of the upper and lower reciprocating members. The distal ends of the upper and lower reciprocating members may extend past the distal end of the handle such that the distal ends of the upper and lower reciprocating members may be pressed together to create a smaller profile for entry into the facet capsule and in between the first and second articulating subchondral surfaces. The entry into the facet capsule may result in extension of the proximal ends of the upper and lower reciprocating members away from the handle, wherein the proximal ends of the upper and lower reciprocating members are configured be articulated toward the handle, the hinge acting as a fulcrum to separate the distal ends of the upper and lower reciprocating members and distract the first and second articulating subchondral surfaces.

Generally, the distal ends of the upper and lower reciprocating members may be sized to be delivered into the facet cavity through an aperture in the facet capsule.

In one embodiment, the handle may comprise a hollow tube, with a shaft running through the tube to the distal end of the handle, and a rasp coupled to the shaft at the distal end of the handle, wherein the shaft may be reciprocated within the tube such that the rasp runs along a subchondral surface to decorticate the surface.

Another aspect of an embodiment is an introducer for delivering an implant to an interior region of a facet joint, comprising an elongate handle having a proximal end and a distal end, and a spatula-shaped tip disposed at the distal end of the handle, the tip comprising upper and lower parallel planar surface extending distally outward from the distal end of the handle. The tip may be sized to be delivered into the facet joint via an aperture in the joint capsule and oriented in the joint substantially in line with the plane of the facet joint articulating surfaces, and comprises a platform configured to receive the implant and deliver the implant to a location within the cavity.

In one embodiment, the implant may comprise an inflatable membrane with a pocket configured to slide over the distal tip of the introducer. In this case, the introducer has a delivery line extending from the proximal end of the handle to distal tip and being configured to dispense an inflation medium to the inflatable membrane.

Another aspect of an embodiment is an apparatus for delivering an agent to an interior region of a facet joint, having an elongate handle with a proximal end and a distal end, and a shaft extending from the distal end of the handle. The shaft has a beveled surface at its distal tip, and a delivery line extending from the proximal end of the handle to the distal tip of the shaft. The beveled distal tip of the shaft may be sized to be delivered into the facet joint via an aperture in the joint capsule and oriented in the joint to deliver the agent to a treatment location within the joint. A blade may also be included on the distal end of the shaft, the blade configured to facilitate access into the facet joint.

In one embodiment of the current aspect, the shaft may comprise a lower planar surface extending proximally from the distal tip, wherein the lower planar surface provides a platform for guiding the apparatus in cooperation with a second instrument through the aperture.

Another aspect of an embodiment is a surgical system for treating the facet joint, comprising a first apparatus configured to gain access to the joint. The first apparatus may have an elongate handle having a proximal end and a distal end, and spatula-shaped tip disposed at the distal end of the handle, the tip comprising upper and lower parallel planar surface extending distally outward from the distal end of the handle. The tip may be sized to be delivered into the facet joint via an aperture in the joint capsule and oriented in the joint substantially in line with the plane of the facet joint articulating surfaces. The lower planar surface may provide a platform for guiding a second instrument through the aperture for treatment of the facet joint. The second instrument may comprise a planar surface that is configured to mate with the planar surface of the first instrument and slide distally along the first instrument to into the facet joint.

Another aspect of an embodiment is a system for facet joint immobilization, comprising: a facet access blade configured to pierce through the facet capsule and into the facet cavity to generate a slit-shaped aperture in the facet capsule that extends substantially parallel to the first and second articulating subchondral surfaces. The system may include a distraction apparatus configured to be delivered through the facet capsule and into the facet cavity to distract the first and second articulating subchondral surfaces a predetermined distance, and a decortication apparatus configured to be delivered through the facet capsule and into the facet cavity to decorticate at least one of the first and second articulating subchondral surfaces a predetermined distance. An introducer may also be delivered through the facet capsule and into the facet cavity to deliver an implant between the first and second articulating subchondral surfaces to immobilize the joint at the predetermined distance.

Another aspect of an embodiment is a method for accessing the facet joint of a patient, comprising: delivering a cutting blade to the facet joint capsule; and piercing through the facet capsule and into the facet cavity with the cutting blade to generate a slit-shaped aperture in the facet capsule, the aperture being oriented and sized to accommodate access into the facet joint The method may further include delivering an introducer through the aperture and into the facet cavity. The cutting blade may be configured to guide delivery of the introducer.

Another aspect of an embodiment is a method for accessing the facet joint of a patient, comprising: delivering a first apparatus configured to gain access to the joint. The first apparatus comprising an elongate handle having a proximal end and a distal end, and a spatula-shaped tip disposed at the distal end of the handle, the tip comprising upper and lower parallel planar surface extending distally outward from the distal end of the handle. The tip is sized to be delivered into the facet joint via an aperture in the joint capsule and oriented in the joint substantially in line with the plane of the facet joint articulating surfaces. A second apparatus is delivered by guiding the second apparatus along the lower planar surface of the first apparatus and through the aperture for treatment of the facet joint. The second apparatus may have a planar surface that is configured to mate with the planar surface of the first apparatus and slide distally along the first apparatus to into the facet joint.

Yet another aspect of an embodiment is a method for immobilizing the facet joint of a patient; comprising delivering a cutting blade to the facet joint capsule; piercing through the facet capsule and into the facet cavity with the cutting blade to generate an aperture in the facet capsule accessing the joint with an introducer; preparing the joint by sanding down cortical bone with a rasp; wherein the rasp is configured to be non-invasively inserted within the aperture created by the cutter; and delivering a distraction device into the facet cavity and distracting the first and second articulating subchondral surfaces.

In one embodiment, the introducer facilitates delivery of the rasp and distraction device.

In one embodiment, the distraction device comprises a wedge detachably disposed at the distal end of an elongate handle, with the method further including delivering the wedge into the cavity through an aperture in the capsule so that the wedge contacts the first and second articulating subchondral surfaces and distract the surfaces as the wedge is driven into the cavity.

In another embodiment, the distraction device comprises an inflatable membrane, and distracting the first and second articulating subchondral surfaces comprises inflating the membrane.

In yet another embodiment, the distraction device comprises a reciprocating introducer, and distracting the first and second articulating subchondral surfaces comprises inserting the introducer into the facet joint and articulating a pair of distal reciprocating members.

Further aspects of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIGS. 3A-3H include several views of a facet access tool according to certain embodiments.

FIGS. 8A-8H include several views of a facet introducer, according to certain embodiments.

FIGS. 11A-11I include several views of a facet distraction device, according to certain embodiments.

FIGS. 12A-H include several views of a detachable wedge used with the facet distraction device of FIGS. 11A-11I.

FIGS. 13A-13G include several views of an alternative facet distraction device, according to certain embodiments.

FIGS. 15A-15G include several views of a facet delivery tool for delivering an injectable biomaterial, according to certain embodiments.

FIGS. 16A-16I include several views of a facet inflatable membrane introducer, according to certain embodiments.

DETAILED DESCRIPTION OF THE INVENTION

Referring more specifically to the drawings, for illustrative purposes, one embodiment of an apparatus is generally shown in FIG. 3A through FIG. 16. It will be appreciated that the apparatus may vary as to configuration and as to details of the parts, and that the method may vary as to the specific steps and sequence, without departing from the basic concepts as disclosed herein.

Figure 1:
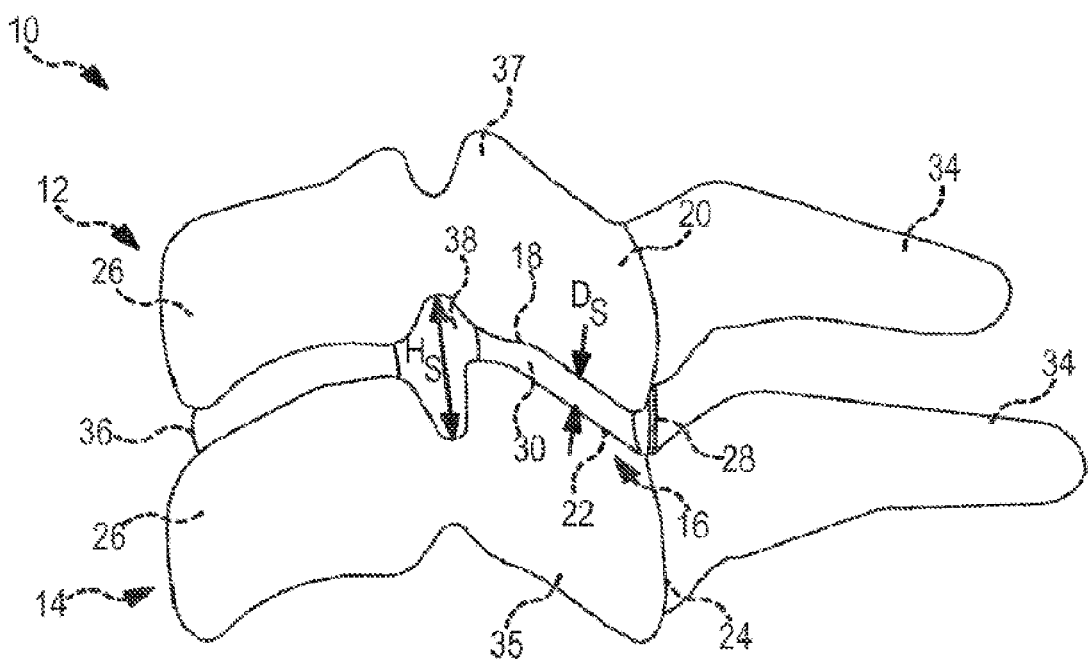
FIG. 1 is a lateral view of two cervical vertebral members in a stenosed condition.

FIG. 1 illustrates a simplified lateral view of a portion of the cervical spine 10. The basic biomechanical unit or motion segment of the spine consists of two adjacent vertebrae 12 and 14 and the three joint articular complex through which they move and are constrained in relation to one another. The spine articulations generally consist of an intervertebral disc 26 located between the vertebral bodies 26 of adjacent vertebrae 12, 14, and two facet joints 16 symmetrically located laterally from the sagittal plane at the posterior end of the vertebral bodies 26.

The facet joints 16 allow constrained spinal motion, while protecting the contained neural structures. From a kinematic viewpoint, the intervertebral facet joints 16 are highly constrained sliding planar articulations, lubricated by synovial fluid contained within the facet joint capsule 30. In the cervical spine, the geometry of the cervical vertebral bodies provides a high degree of protection for the neural elements by limiting normal motion of the spine to within physiologic limits. The upward inclination of the superior articular surfaces of the facet joints allows for considerable flexion and extension, as well as for lateral mobility.

The distraction, preparation and delivery devices disclosed herein facilitate minimally invasive or percutaneous surgical access, distraction and implant delivery to the facet joint, which is advantageous due to reduced surgical time, reduced recovery time, and improved surgical outcome. Each vertebral segment comprises a spinous process 34 located at the posterior end of the vertebrae, with the vertebral body located anteriorly. Each vertebra comprises an inferior articular (or transverse) process 35 and the superior articular process 37 that form four posterior articulating, e.g. opposing subchondral, surfaces: two superior facets 18 and two inferior facets 16. The inferior facet 18 from the inferior articular process 35 of the upper vertebra 12 and the superior facet from the superior articular process 37 of the lower vertebra 14 form the facet joint 16 on each lateral side of the spine.

Located medial to the articular processes 37 and vertebral bodies 26 is an aperture, or intervertebral foramina 38, that serves as a nerve root canal for the spinal nerves and vessels that transmit signals from the spinal chord to respective locations in the body.

Each facet joint 16 is covered by a dense, elastic articular capsule 28, which is attached just beyond the margins of the articular facets 18, 22. The inside of the capsule is lined by a synovial membrane (not shown), which secretes synovial fluid for lubricating the facet joint. The exterior of the joint capsule is surrounded by a capsular ligament (not shown), which may be temporarily repositioned to give access for insertion of the extendable implant of the present invention, described in further detail below. Thus, from a posterior-lateral approach, access to the facet joint 16 is relatively straightforward and well prescribed, as compared to other regions of the spine, which present a higher likelihood of trauma and risk of permanent damage.

It should also be noted that FIG. 1 depicts cervical foraminal stenosis, e.g. loss of height between the adjacent vertebrae 12, 14. As a result of disc 36 herniation and corresponding height loss, the nerve root canal 38, or intervertebral foraminal height, having a value $H_s$, is narrowed relative to that of healthy anatomy. This narrowing of the foraminal height $H_s$ often leads to compression of the spinal cord and nerve roots (not shown), causing radicular symptoms.

As a result of the stenosed foraminal height $H_s$, the height of the facet joint 16, or distance between subchondral articulating surfaces 18 and 22, is also narrowed, (shown as value $D_s$ in FIG. 1). This may pose complications in the facet joint 16 as well. However, because the height of the disc will be relatively fixed, an increase in the facet joint height will also have a corresponding increase in foraminal height, as described in greater detail below.

Figure 2:
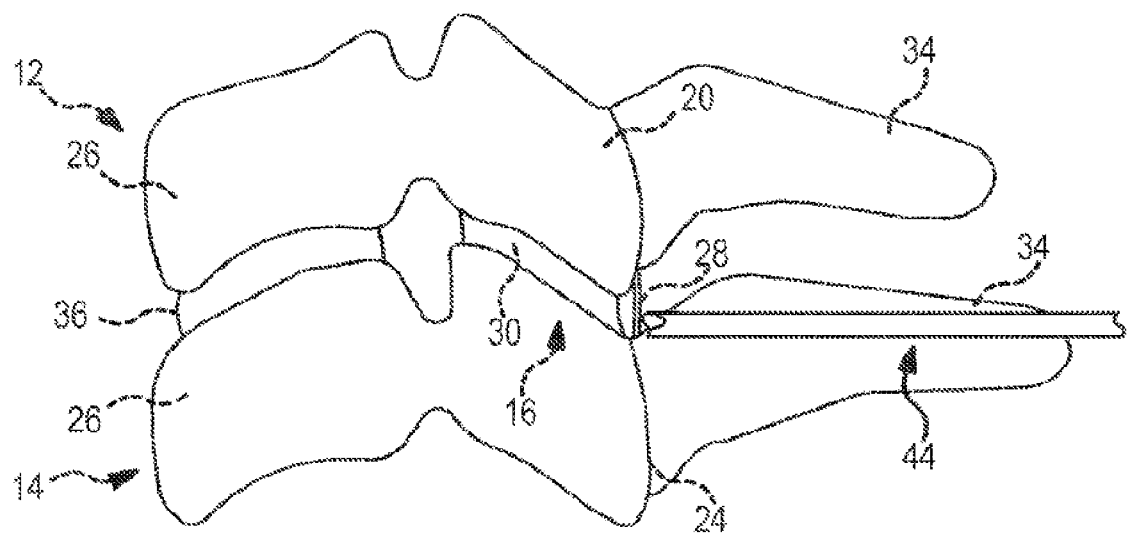
FIG. 2 is a view of a traditional introducer needle being inserted into the facet joint of the vertebral members.
Figure 3E:
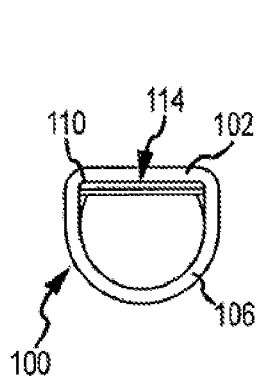
Figure 3F:
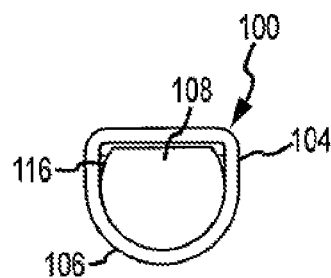
Figure 3G:
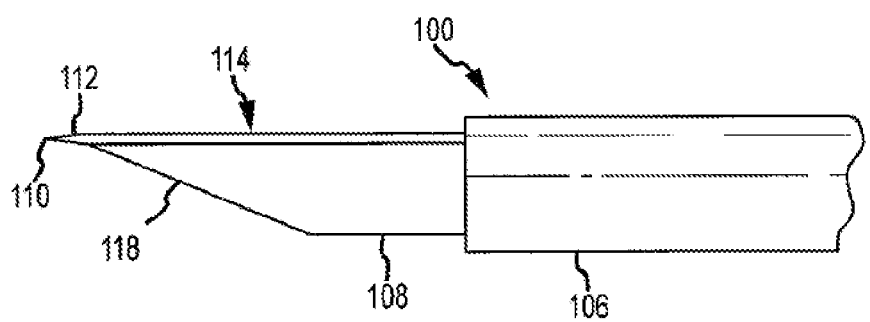
Figure 3H:
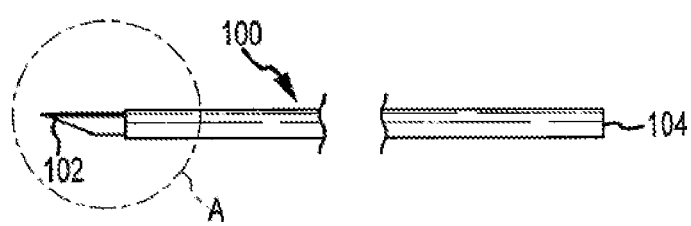

FIG. 2 illustrates a typical procedure for accessing the facet joint using a standard discography introducer needle 44 to access the facet joint. Because the gap or cavity 30 bound between subchondral articulating surfaces 18 and 22 is generally planar, the cylindrical needle 44 may be difficult to navigate into the capsule 30. Generally precise alignment and orientation of the needle 44 with the subchondral surface 18 and 22 may be used for the needle to enter the cavity 30. Thus, the shape and size constraints of the facet joint 16 make typical cylindrical needles 44 difficult to predictably and consistently gain access to the facet joint capsule.

FIGS. 3A-16 show a system and method of the present invention for performing a minimally invasive procedure configured to distract one or more of the facet joints 16 of vertebrae 12, 14, thereby increasing the dimension of the neural foramen while retaining facet joint mobility. One of the major advantages of minimally invasive surgery is the ability to perform the procedure with minimal tissue trauma. Television image intensifier fluoroscopy may be used to provide guidance for surgeon placement of instrumentation and implants precisely to the desired anatomic target in the facet joint 16. The radiographic landmarks are well taught and the relative procedural difficulty of this technique is low.

FIGS. 3A-3H illustrate a facet access tool 100 in accordance with certain embodiments. Tool 100 comprises an elongate handle having a flat cutting blade 112 on its distal end 102. The blade 112 generally comprises a straight, flat (i.e. planar), leading edge 110 at distal tip 102 that is sharpened to allow for piercing of the facet joint capsule 28. Although the leading edge 110 is shown as a straight-line surface when viewed from above in FIG. 3B, it is appreciated that different shapes may also be utilized, (e.g. arcuate, triangular, etc.)

The blade 110 is coupled to shaft 108 that is received inside a central channel 116 running axially down handle 106. The shaft and blade protrude distally from the handle 106 so that flat surface 114 running along the bottom of the blade 112 is exposed. The flat surface 114 facilitates introduction and cooperation of additional instruments used for the procedure, discussed in further detail below.

The shaft 108 has a beveled surface 118 that terminates at a point on the distal tip 102 of blade 112. As will be described in further detail below, the beveled surface 118 allows the blade 112 to access into the facet joint from sub-optimal angles of entry, and wedge the blade 112 into the joint for treatment.

It is appreciated that blade 112 may be a separable from shaft 108 and joined with an adhesive, fastener or other securing means. Alternatively blade 112 and shaft 108 may comprise one contiguous or integral piece of material. The blade and shaft may comprise a hardened metal, such as stainless steel or titanium.

The blade 112 and shaft 108 correspondingly have a D-shaped cross-section. Accordingly, chamber 116 of handle 106 also has a D-shaped cross-section, and is sized to receive shaft 108 and blade 112 with a snug fit. Handle 106 may comprise a plastic or similar polymer that is extruded, molded, or heat-shrunk in shape.

Figure 4:
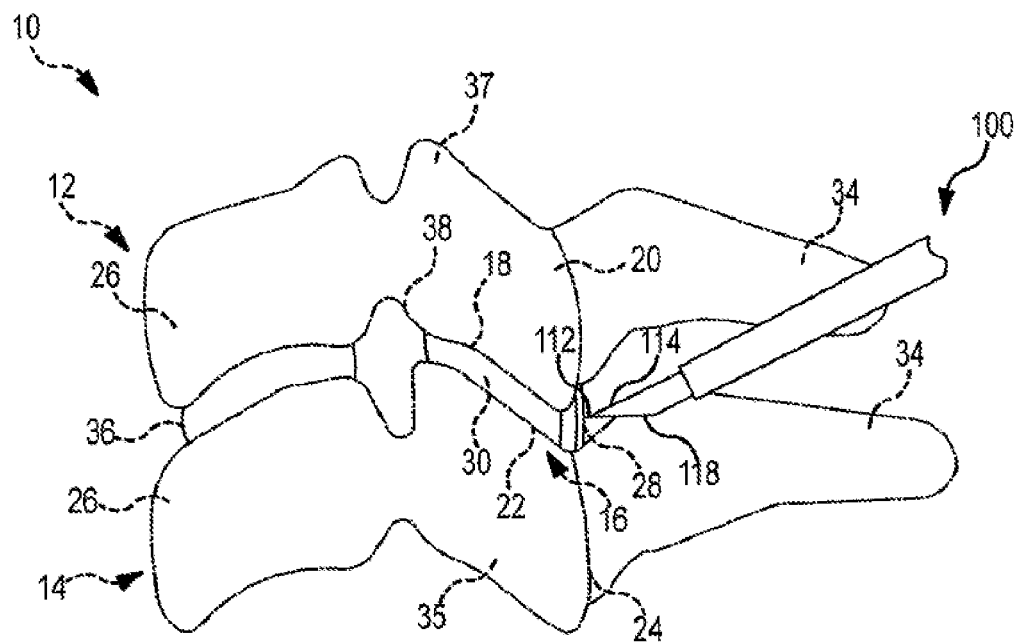
FIG. 4 is a schematic lateral view of the facet access tool of FIGS. 3A-3H positioned at the facet joint capsule of two cervical vertebral members.
Figure 5:
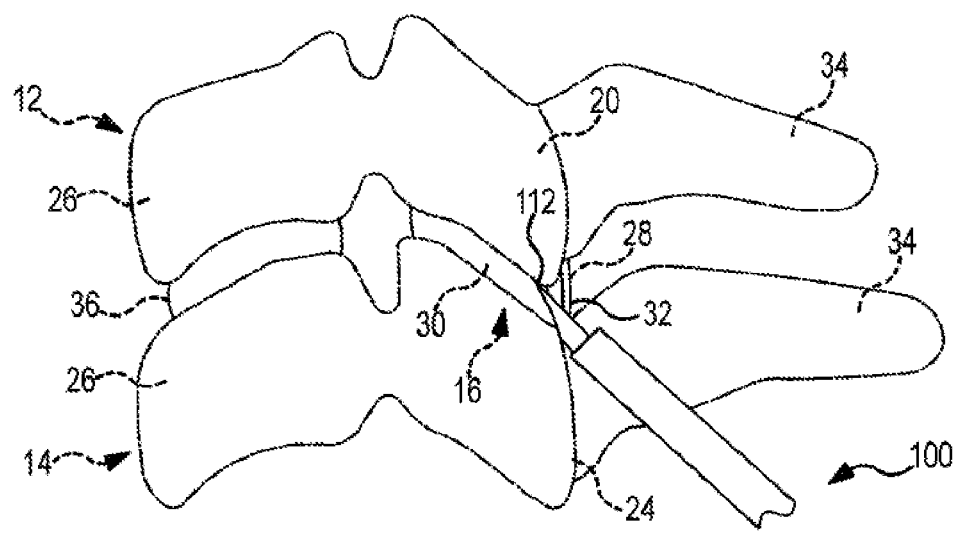
FIG. 5 is a schematic lateral view of the facet access tool of FIGS. 3A-3H piercing and being manipulated within the facet joint capsule, according to certain embodiments.

FIG. 4 illustrates lateral views of facet access tool 100 positioned at the facet joint 16. According to the method of the present invention, the blade 112 is positioned at the desired location facet joint capsule 28 and then pushed into the capsule to generate an opening 32. FIG. 5 shows the access tool 100 manipulated in the facet cavity 30 through the opening 32 in the capsule wall 28.

Figure 6:
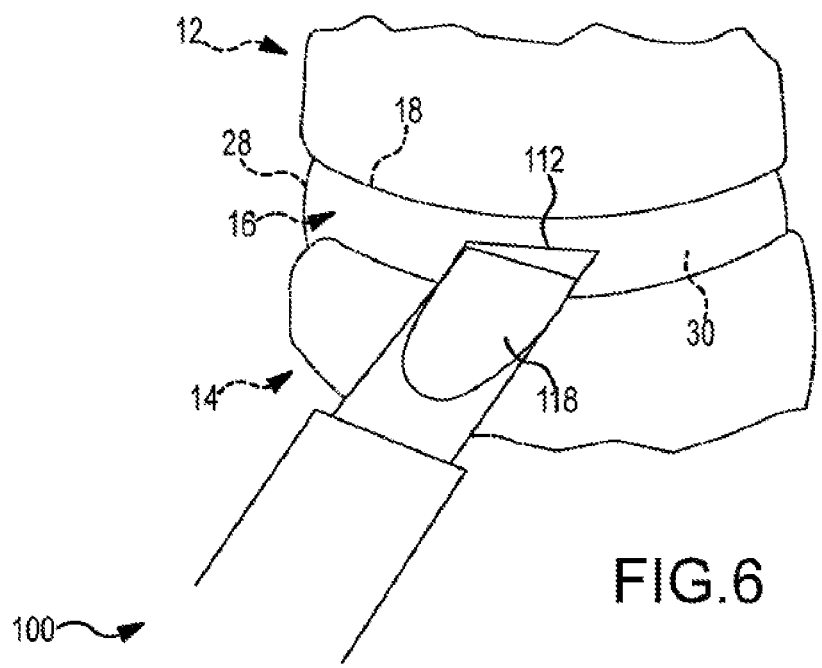
FIG. 6 is another view of the of the facet access tool of FIGS. 3A-3H piercing the facet joint capsule, according to certain embodiments.
Figure 7:
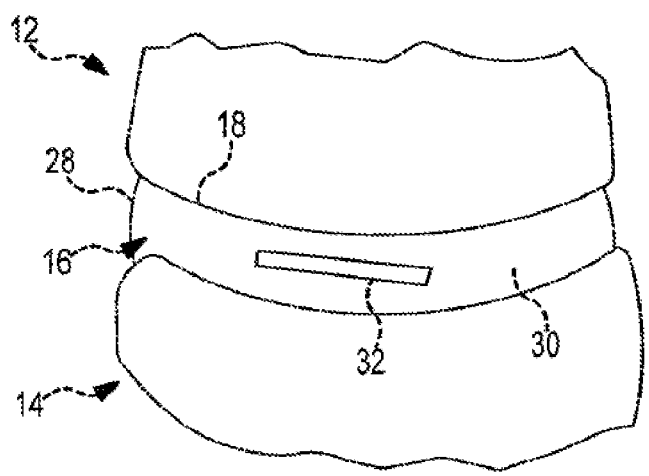
FIG. 7 is a view of the slit-shaped aperture created by the facet access tool of FIGS. 3A-3H.
Figures 8E, 8F:
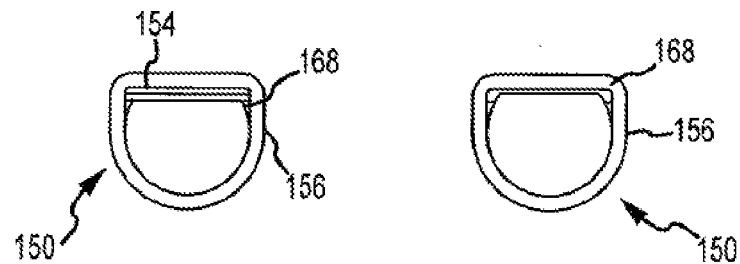
Figure 8G:
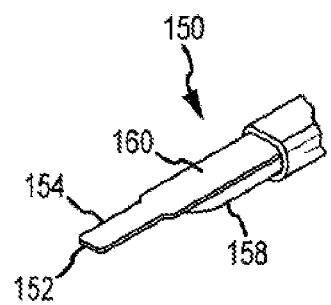
Figure 8H:
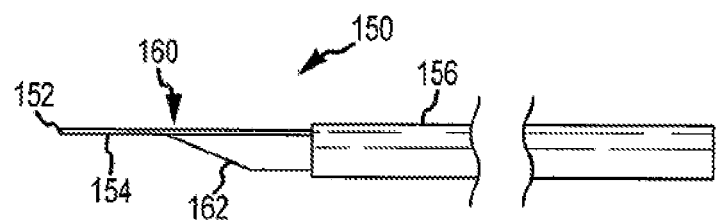

FIGS. 6 and 7 illustrate a postero-lateral view of the incision created by the access tool. As seen in FIG. 7 a slit-like opening 32 is generated that runs generally parallel to the facet joint articular surfaces 18, 22.

Once we have gained access to the facet joint cavity 30 with the cutting blade of the facet access tool 100, an introducer 150 may be inserted into the joint. The introducer 150, illustrated in FIG. 8, comprises a handle 164 at its proximal end, and a malleable "spatula" shaped tip 154 at its distal end 152.

The tip 154 generally comprises a straight, flat leading edge 110 at distal end 152. Although the leading edge 152 is shown as a straight-line surface when viewed from above in FIG. 8A, it is appreciated that different shapes may also be utilized, (e.g. arcuate, triangular, etc.)

The tip 254 is coupled to shaft 158 that is received within a D-shaped opening channel 168 of the handle 156. The shaft 158 and tip 154 protrude distally from the handle 156 so that flat surface 160 running along the bottom of the tip and shaft is exposed. The shaft 158 has a beveled surface 162 that terminates at a point proximal to the distal tip end 152 of tip 154.

The malleable and thin planar shape of the "spatula" tip 154 and beveled shaft 158 allow for suboptimal entry angles and compensates for the narrow spacing of the facet joint. In the method of the present invention, the tip 154 is inserted into the opening 32 created by the facet access tool 100. The flat, thin cross-section of tip 154 is configured to easily slide into thin, planar cavity 30 of the facet joint 30.

Figure 9:
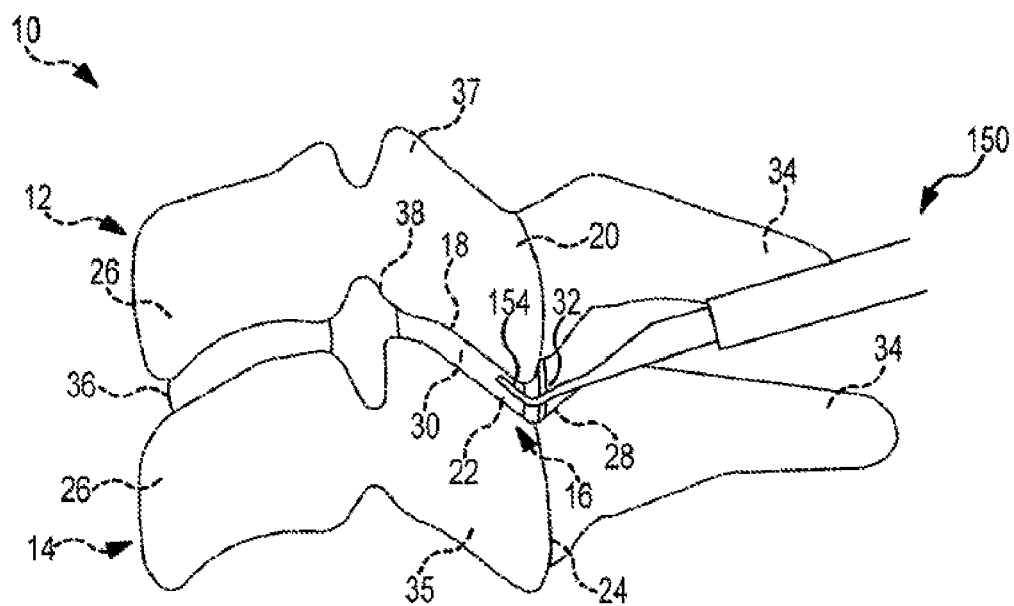
FIG. 9 is a schematic lateral view of the introducer tool of FIGS. 8A-8H being manipulated within the facet joint capsule, according to certain embodiments.

As shown in FIG. 9, the tip 154 of introducer is malleable so that it bends into the cavity 30 if introduced from a sub optimal angle. This, along with the beveled surface 162, allows the blade introducer 150 to access into the facet joint from sub-optimal angles of entry, and wedge or manipulate the introducer 150 into the proper orientation in the joint 16 for treatment.

Figure 10:
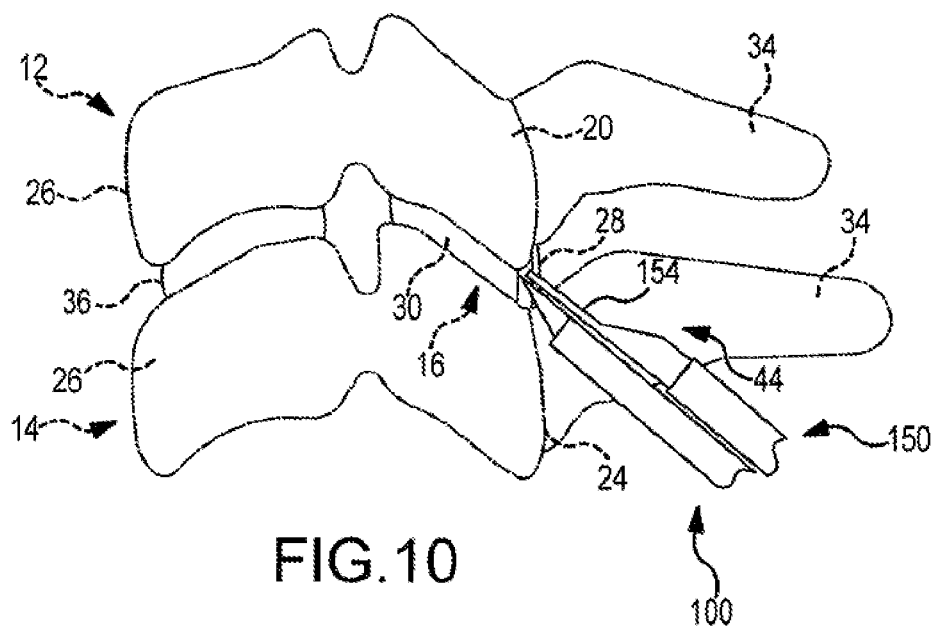
FIG. 10 is a schematic lateral view of the facet blade being used to guide the introducer tool of FIGS. 8A-8H into the joint capsule, according to certain embodiments.
Figure 11F:
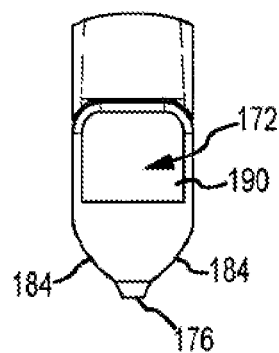
Figure 11G:
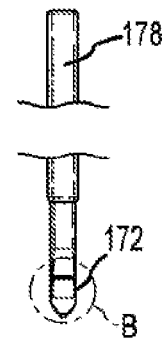
Figure 11H:
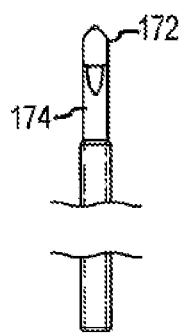
Figure 11I:
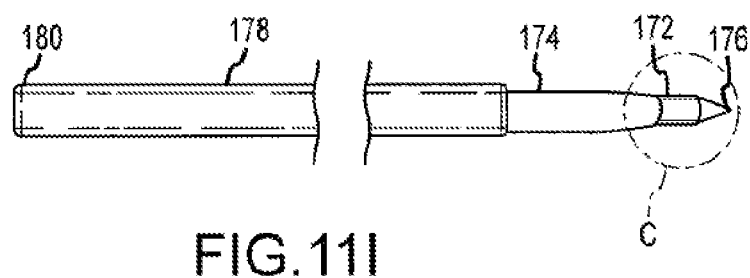
Figure 12H:
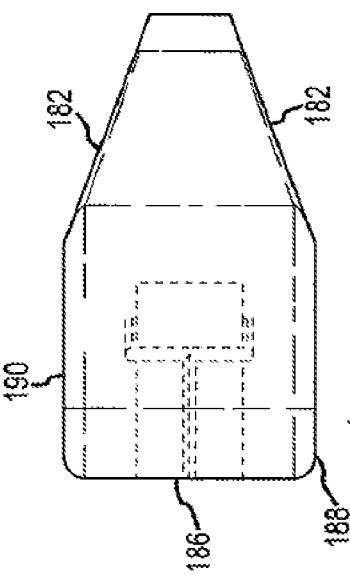
Figure 12G:
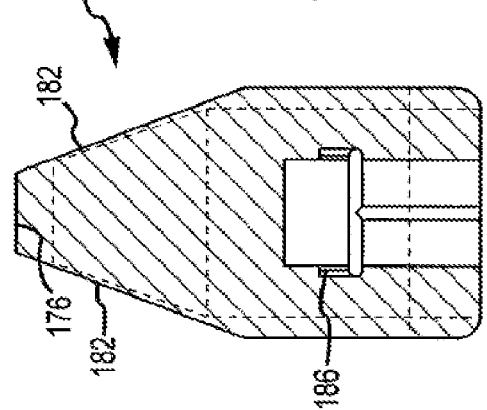
Figure 12F:
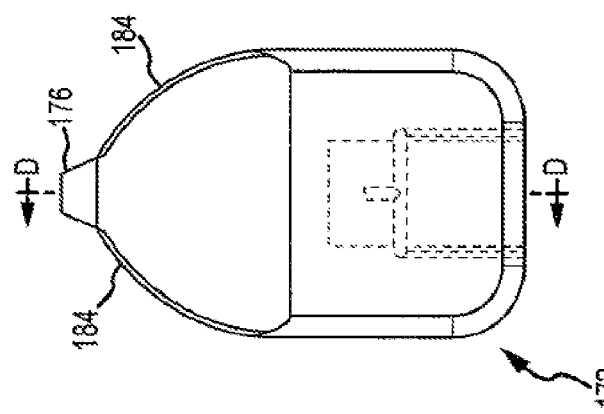
Figure 13A:
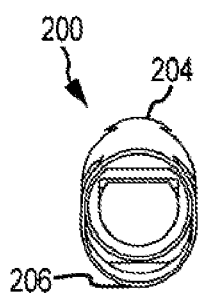
Figure 13B:
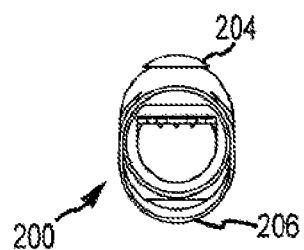
Figure 13C:
Figure 13D:
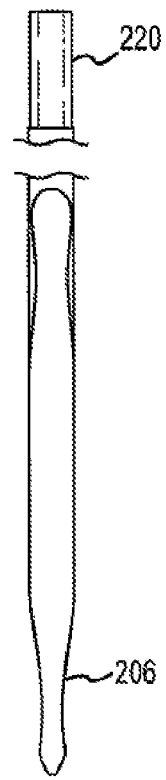
Figure 14A:
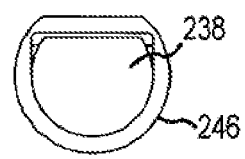
FIGS. 14A-14I include several views of a facet decortication tool, according to certain embodiments.
Figure 14B:
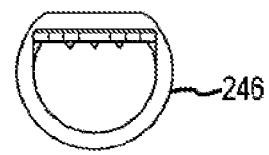
Figure 14C:
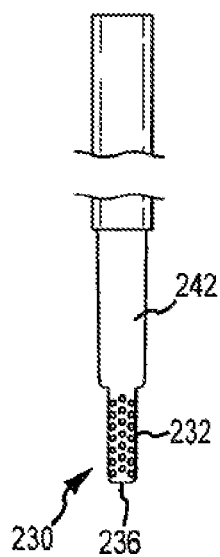
Figure 14D:
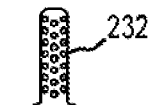
Figure 14D:
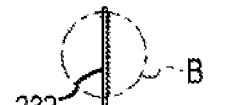
Figure 14D:
Figure 14E:
Figure 14F:
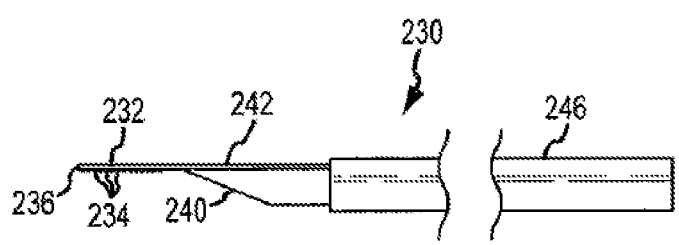
Figure 14G:
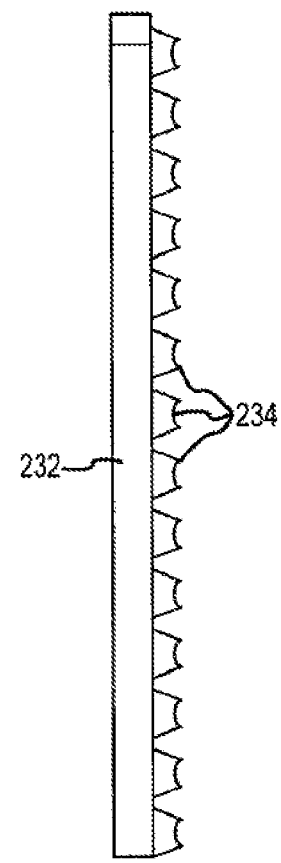
Figure 14H:
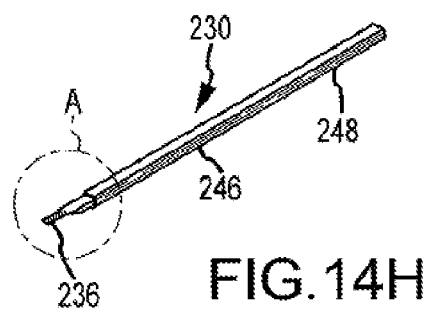
Figure 14I:
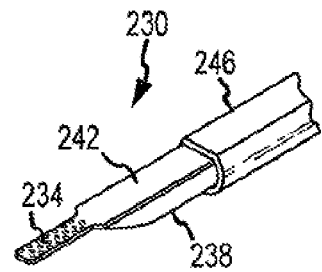
Figure 15A:
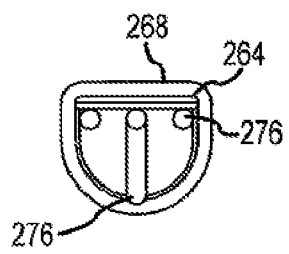
Figure 15B:
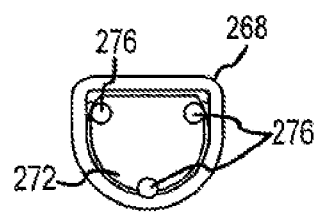
Figure 15C:
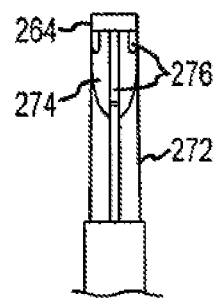
Figure 15C:
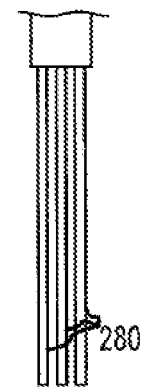
Figure 15D:
Figure 15D:
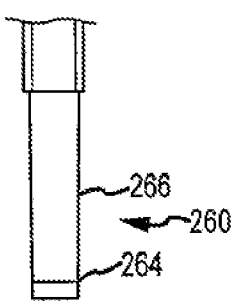

The introducer 150 may be inserted into the cavity 30 after the access blade 100 has been removed, or may be inserted while the access blade 100 is still in place, essentially using the access blade to guide the introducer 150 by sliding the flat bottom surface 160 along the bottom surface 114 of the access blade, as shown in FIG. 10.

In a similar fashion as illustrated in FIG. 10 with the access blade 100, the flat tip 154 of the introducer is also configured to provide a point of entry for later devices used in the surgical method of the present invention, e.g. to enable distraction, decortication, decompression, and fusion of the facet joint 16.

With proper access and orientation of the instruments in the facet joint 16, the articular surfaces 18 and 22 may be distracted to increase the distance $D_s$. Distraction of the joint 16 may be accomplished via a number of methods, including use of an inflatable membrane such as that disclosed in U.S. patent application Ser. No. 11/618,619 filed on Dec. 29, 2006, herein incorporated by reference in its entirety.

Referring now to FIGS. 11A-11I and 12A-12H, distraction may be achieved via a wedge-inserter 170. The wedge inserter 170 comprises an elongate handle 178 at its proximal end 180 and detachable wedge-shaped tip 172 disposed on shaft 174 that is encased, at least proximally, within the handle 178.

The detachable tip 172, further illustrated in FIGS. 12A-12H, converges to a nipple 176 at the distal extremity via beveled surfaces 182 and lateral arcuate surfaces 184. The detachable tip 172 has a keyed receiving hole 186 for attaching the tip 172 to the shaft 174.

The upper and lower beveled surfaces 182 converge to nipple 176 from a box shaped platform defined by lower and upper parallel distraction surfaces 188, and 190. The distance between the lower and upper distraction surfaces 188, and 190 sets the thickness T of the wedge.

The inserter 170 may be directed into to the facet joint cavity 30 with guidance from sliding it along introducer 150. When inserted into the cavity 30, the inserter generates an outward compressive force on the subchondral surfaces 18 and 22 to increase the distance between them to a desired treatment or nominal value $D_T$. As shown in FIGS. 12B-12D, a set of tips 192, 194 and 196, all having a different thickness T, may be used in series so that the joint is progressively distracted. The final thickness T will correspond to the treatment or nominal value $D_T$.

This distraction of walls 18 and 22 correspondingly increases the height of the intervertebral foramin to a treatment or nominal value $H_T$. The value of $D_T$, and resulting increase in $H_T$ may be predetermined by the surgeon prior to the surgery based on pre-op analysis of the patient's condition and anatomy, and/or may also be iteratively devised by patient feedback of symptom improvement during the procedure.

Referring now to FIGS. 13A-13G, distraction may also be achieved via duck-billed distraction device 200. The duckbill comprises an upper pivoting member 204 and lower pivoting member 202 mounted to a tube 214 at hinge 206. A rasp 208 is mounted on shaft 220 that is slideably received within the tube 214.

The distal tips 210 of the pivoting members 202, 204 are configured to collapse down over rasp 208 to facilitate entry of the duckbill into the facet joint cavity 30. Correspondingly, the proximal ends 212 of the pivoting members 202, 204 expand outward from tube 214. Once properly positioned within the cavity 30, the proximal ends of the pivoting members 202, 204 (which are in an expanded configuration), can be manually pressed inward toward the shaft 214. This activation causes the duckbill to expand at distal tips 210, and distract the facet joint 16.

With the facet joint surfaces 18, 22 distracted, the rasp 232 may be articulated distally outward from the duckbill and on to the facet surfaces 18, 22. The rasp 208 may be reciprocated back and forth within the tube 214 (via manual manipulation of the proximal end of shaft 220), thereby decorticating (by sanding or grating the surface) the surfaces in preparation for fusion.

FIGS. 14A-14I illustrate a standalone decorticator 230. Decorticator 230 comprises a flat, flexible spatula-shaped rasp 232 at its distal end 236. The rasp 232 is coupled to shaft 238 that is received inside a central channel running axially down handle 246. The shaft and rasp protrude distally from the handle 246 so that flat surface 242 running along the bottom of the rasp 232 is exposed. The flat surface 242 facilitates introduction and cooperation with the introducer 150 described above.

The shaft 238 has a beveled surface 240 that terminates at a point proximal to the distal tip 236 of the rasp 232. The thin, flexible shape allows the rasp to bend and access into the facet joint from sub-optimal angles of entry. The rasp may have one or more surfaces comprise a plurality of teeth 234 configured to grate down the hard cortical surface of the opposing facet joint surfaces 18, 22.

Alternative decorticating devices may include a flat device with an aggressive cutting surface that is rolled to achieve roughening of the facet surface (not shown), and a device with two opposing rasp surfaces that articulate in a lateral motion through a "scissor like" activation feature. In such a configuration, the two blades of the scissors have flat upper and lower roughened surfaces that would simultaneously decorticate the opposing subchondral surfaces by remote manipulation of the blades. In other embodiments, decorticating devices may take the form of an abraded shaft and decorticating may be performed by rolling the device. In yet other embodiments, decorticating device may take the form of a file mechanism and decorticating may be performed with a back and forth filing motion, where the decorticating device is positioned and actuated using floss.

With the facet joint 16 distracted and decorticated, the method of the present invention includes an embodiment where a specifically shaped piece of structural bone allograft (not shown) is then inserted into the space of distraction between the opposing facet joint surfaces. The bone allograft may be one of a series or kit of bone allograft having a predetermined shape and size (e.g. be sized in thickness that vary by small increments). The bone allograft may then be further shaped by the physician to have a custom size and shape correlating to the specific anatomy of the patient to be treated.

The bone allograft is further supplemented with an injectable biomaterial such as bone morphogenic protein (BMP) to supplement the fusion potential at this level. FIGS. 15A-15G illustrate an injection device 260 for injecting BMP or like substances in accordance with the present invention. In some embodiments, the injectable biomaterial is used alone without a bone allograft. In either case, the injectable biomaterial may take the form of BMP as mentioned or other injectable biomaterials such as, but not limited to OP1, bonegraft, stem cells, bone cement (PMMA), or other injectable biomaterials now known or later developed.

Device 260 includes an elongate handle 268 having a flat cutting blade 264 on its distal end 262. The blade 264 generally comprises a straight, flat (i.e. planar), leading edge at distal tip 262. Although the leading edge 262 is shown as a straight-line surface when viewed from above in FIG. 15C, it is appreciated that different shapes may also be utilized, (e.g. arcuate, triangular, etc.)

The blade 264 is coupled to shaft 272 that is received inside a central channel running axially down handle 268. The shaft and blade protrude distally from the handle 268 so that flat surface 266 running along the bottom of the blade 262 is exposed. The flat surface 266 facilitates introduction and cooperation with additional instruments such as introducer 150.

The shaft 272 has a beveled surface 274 that terminates at a point on the distal tip 262 of blade 264. The beveled surface 274 allows the blade 112 to access into the facet joint from sub-optimal angles of entry, and wedge the blade into the joint for treatment.

The blade 264 and shaft 272 correspondingly have a D-shaped cross-section. Accordingly, the chamber of handle 268 also has a D-shaped cross-section, and is sized to receive shaft 272 and blade 264 with a snug fit.

The shaft has one or more channels 276 that run axially down the length of the shaft to deliver an injectable biomaterial from lines 280 located at the proximal end 270 of handle 268 to the distal tip 262 of the device. Thus, with the distal tip 262 positioned in the facet joint cavity 230, bmp is delivered though channels 276 to distal tip 262 at the treatment site.

Distraction may also be accomplished via insertion of an inflatable membrane in the joint 16. FIGS. 16A-16I illustrate an insertion device 300 for inserting inflatable membrane 302 into the facet joint in accordance with the present invention.

The insertion device 300 comprises a handle 316 at its proximal end 318, and a malleable "spatula" shaped tip 306 at its distal end 308.

The tip 306 generally comprises a straight, flat leading edge at distal end 308. Although the leading edge 308 is shown as a straight-line surface when viewed from above in FIG. 16A, it is appreciated that different shapes may also be utilized, (e.g. arcuate).

The tip 306 is coupled to shaft 310 that is received within a D-shaped opening channel of the handle 316. The shaft 310 and tip 306 protrude distally from the handle 316 so that flat surface 314 running along the bottom of the tip and shaft is exposed. The shaft 310 has a beveled surface 312 that terminates at a point proximal to the distal tip end 308 of tip 306.

Inflatable membrane 302, in accordance with the present invention, has a pocket 304 such that the inflatable membrane 302 can be disposed on distal end 308, and delivered through opening 32 created by the access tool 100 and into the cavity 30. Delivery into the cavity may be guided by sliding lower surface 314 along introducer 150. Once the inflatable membrane 302 is positioned in the proper location within cavity 30, inflation medium is delivered through line 330 running axially along shaft 310 from proximal end 318 to distal tip 308, and the inflatable membrane 302 is expanded inside the joint 30. The inflatable membrane 302 generates a force on the opposing facet surfaces and distracts the joint. With the added pressure, the insertion device 300 is simply just pulled out of the joint, with the tip 306 sliding out of pocket 304 while the inflatable membrane 302 retains its position.

The malleable and thin planar shape of the "spatula" tip 306 and beveled shaft 312 allow for suboptimal entry angles and compensates for the narrow spacing of the facet joint. Thus, the inflatable membrane 302 may be delivered from a less invasive, by non-aligned orientation.

The delivered implant is configured to distract the joint and reverse narrowing of the nerve root canal 38 and alleviate symptoms of cervical stenosis. However, it is also within the scope of the present invention to size the implant according to other spinal conditions, for example to correct for cervical kyphosis or loss of cervical lordosis The process for achieving indirect cervical decompression and fusion may also include posterior stabilization with any number of commercially available implants & instrument sets available in the art.

Although the embodiments disclosed above are directed primarily to installation in the cervical facet joint, it is contemplated that the devices and methods may also be used to increase foraminal dimension in other regions of the spine, e.g. thoracic, lumbar, etc.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A method of accessing a facet joint to prepare the joint for delivery of an implant between a first and second articulating subchondral surface of the facet joint, the method comprising:
   accessing the facet joint from a posterior-lateral approach with a facet access tool, the facet access tool comprising:
   an elongate handle having a proximal end and a distal end; and
   a capsule piercing portion disposed at the distal end of the handle, the capsule piercing portion comprising a flat leading edge; and
decorticating the facet joint with a decortication apparatus to prepare the joint for delivery of an implant between the first and second articulating subchondral surfaces of the facet joint, wherein the decortication apparatus comprises a flat, spatula shaped rasp configured to decorticate at least one of the articulating surfaces.

2. The method of claim 1, wherein the decortication apparatus further comprises a shaft attached to the rasp and includes a distal, beveled surface.

3. The method of claim 1, wherein the decortication apparatus comprises a flat device configured to decorticate at least one of the articulating surfaces.

4. The method of claim 1, wherein the implant comprises bone allograft.

5. A method of preparing a facet joint for delivery of an implant between the first and second articulating subchondral surfaces of the facet joint from a posterior-lateral approach, the method comprising:
   accessing the facet joint with a facet access tool; and
   decorticating the facet joint with the decortication apparatus to prepare the facet joint for an implant, the decortication apparatus comprising a flat, spatula shaped rasp with a distal beveled surface and configured to decorticate at least one articulating surface, the decortication apparatus further comprising a shaft attached to the rasp.

6. The method of claim 5, wherein the implant comprises bone allograft.

* * * * *